(12) United States Patent
Schymitzek et al.

(10) Patent No.: US 10,941,370 B2
(45) Date of Patent: Mar. 9, 2021

(54) TRANSPARENT TEXTILE CARE AGENT

(71) Applicants: Henkel AG & Co. KGaA, Duesseldorf (DE); BASF SE, Ludwigshafen (DE)

(72) Inventors: Tatiana Schymitzek, Krefeld (DE); Simon Pluszynski, Duesseldorf (DE); Ulrich Platzbecker, Duesseldorf (DE); Peter Schmiedel, Duesseldorf (DE); Roland Ettl, Altlussheim (DE); Silvia Martinez Barrachina, Aribau (ES); Nuria Bonastre Gilabert, Barbera del Valles (ES); Maria Escoda Margenat, St. Just Desvern (ES)

(73) Assignees: Henkel AG & Co. KGaA, Duesseldorf (DE); BASF SE, Ludwigshafen (DE)

(*) Notice: Subject to any disclaimer, the term of this patent is extended or adjusted under 35 U.S.C. 154(b) by 640 days.

(21) Appl. No.: 15/328,759

(22) PCT Filed: Jul. 15, 2015

(86) PCT No.: PCT/EP2015/066172
§ 371 (c)(1),
(2) Date: Jan. 24, 2017

(87) PCT Pub. No.: WO2016/012327
PCT Pub. Date: Jan. 28, 2016

(65) Prior Publication Data
US 2017/0218304 A1 Aug. 3, 2017

(30) Foreign Application Priority Data
Jul. 25, 2014 (DE) .................... 10 2014 010 875

(51) Int. Cl.
| | | |
|---|---|---|
| *C11D 3/00* | (2006.01) |
| *C07C 213/08* | (2006.01) |
| *C11D 1/62* | (2006.01) |
| *C11D 3/22* | (2006.01) |
| *C11D 11/00* | (2006.01) |
| *D06M 15/03* | (2006.01) |
| *D06M 15/09* | (2006.01) |
| *C11D 3/37* | (2006.01) |
| *D06M 13/463* | (2006.01) |
| *C11D 17/00* | (2006.01) |
| *D06M 15/267* | (2006.01) |
| *D06M 15/53* | (2006.01) |
| *C11D 1/835* | (2006.01) |
| *C07C 213/02* | (2006.01) |
| *D06M 15/285* | (2006.01) |
| *C07C 213/06* | (2006.01) |
| *C11D 3/30* | (2006.01) |
| *C11D 3/382* | (2006.01) |

(52) U.S. Cl.
CPC .......... *C11D 3/0015* (2013.01); *C07C 213/02* (2013.01); *C07C 213/06* (2013.01); *C07C 213/08* (2013.01); *C11D 1/62* (2013.01); *C11D 1/835* (2013.01); *C11D 3/222* (2013.01); *C11D 3/30* (2013.01); *C11D 3/3773* (2013.01); *C11D 3/382* (2013.01); *C11D 11/0017* (2013.01); *C11D 17/003* (2013.01); *D06M 13/463* (2013.01); *D06M 15/03* (2013.01); *D06M 15/09* (2013.01); *D06M 15/267* (2013.01); *D06M 15/285* (2013.01); *D06M 15/53* (2013.01); *D06M 2200/50* (2013.01)

(58) Field of Classification Search
CPC ........................... C11D 3/0015; C07C 213/06
See application file for complete search history.

(56) References Cited

U.S. PATENT DOCUMENTS

| | | | |
|---|---|---|---|
| 5,349,106 A | 9/1994 | Behler et al. | |
| 5,397,507 A * | 3/1995 | Bauer | C11D 1/72 510/357 |
| 5,670,677 A | 9/1997 | Ponsati Obiols et al. | |
| 5,880,299 A * | 3/1999 | Ponsati Obiols | A61K 8/44 554/103 |
| 6,165,946 A * | 12/2000 | Mueller | C09K 8/28 507/203 |
| 6,300,307 B1 * | 10/2001 | Bermejo | C07C 219/06 510/499 |

(Continued)

FOREIGN PATENT DOCUMENTS

| | | |
|---|---|---|
| DE | 4409322 C1 | 4/1995 |
| DE | 19751151 A1 | 5/1999 |

(Continued)

OTHER PUBLICATIONS

AkzoNobel Surface Chemistry. (Year: 2016).*
Bilbo, R. et al., "Amphoteric Surfactants; A Structure Function Study," Soap/Cosmetics/Chemical Specialties for Apr. 1990, pp. 46, 48, 50, 114 & 116.
Ellis, P.R. et al., "Amphoteric Surfactants—The Next Generation," Euro Cosmetics, pp. 14-16.
Griffin, W.C., "Classification of Surface-Active Agents by "HLB"," Journal of the Society of Cosmetic Chemists, 1949, pp. 311-326.
Griffin, W.C., "Calculation of HLB Values of Non-Ionic Surfactants," Journal of the Society of Cosmetic Chemists, 1954, pp. 249-256.
Holzman, S., et al. "Amphoteric Surfactants—Amphoteric Surfactants of the Amphoglycinate and Amphocarboxyglycinate Type," Tenside Detergents 1986, pp. 309-313.

(Continued)

*Primary Examiner* — Mark Eashoo
*Assistant Examiner* — M. Reza Asdjodi
(74) *Attorney, Agent, or Firm* — Lorenz & Kopf, LLP

(57) ABSTRACT

The present disclosure relates to textile care agents and to optically clear and transparent fabric softener formulations which also have a viscous consistency, containing a combination of special ester quats with nonionic emulsifiers and cationic thickeners, to the use of said textile care agents and fabric softener formulations. The present disclosure also relates to a method for washing textiles using said textile care agent and fabric softener formulations. The present disclosure relates to methods for producing the special ester quats, to the thus resulting ester quats and to the use thereof.

20 Claims, No Drawings

(56) References Cited

U.S. PATENT DOCUMENTS

| | | | |
|---|---|---|---|
| 6,432,895 B1* | 8/2002 | Bigorra | A61K 8/416 510/119 |
| 6,465,419 B1* | 10/2002 | Bermejo Oses | A61K 8/45 510/504 |
| 8,563,498 B2* | 10/2013 | Gizaw | C11D 3/001 510/475 |
| 8,765,154 B2 | 7/2014 | Bigorra Llosas et al. | |
| 2003/0130162 A1* | 7/2003 | Llosas | A61K 8/345 510/515 |
| 2004/0213997 A1* | 10/2004 | Bonastre Gilabert | C11D 3/0015 428/402 |
| 2006/0070189 A1* | 4/2006 | Raehse | C11D 3/382 8/115.51 |
| 2006/0135399 A1* | 6/2006 | Grandmaire | C11D 1/62 510/515 |
| 2008/0214776 A1* | 9/2008 | Bigorra Llosas | C07C 219/06 528/335 |
| 2012/0137448 A1* | 6/2012 | Panandiker | C11D 1/62 8/137 |
| 2012/0142579 A1* | 6/2012 | Panandiker | C11D 1/62 510/516 |
| 2013/0065813 A1* | 3/2013 | Miravet Celades | C11D 3/0015 510/516 |
| 2016/0024432 A1* | 1/2016 | Sivik | C11D 3/001 8/137 |
| 2017/0218304 A1* | 8/2017 | Schymitzek | D06M 15/03 |

FOREIGN PATENT DOCUMENTS

| | | | | |
|---|---|---|---|---|
| EP | 1136471 | A1 | | 9/2001 |
| EP | 1964832 | A1 | * | 9/2008 ........... C07C 219/06 |
| EP | 1964832 | A1 | | 9/2008 |
| FR | 1156513 | A | | 5/1958 |
| GB | 839407 | | | 6/1960 |
| GB | 873214 | | | 7/1961 |
| GB | 962919 | | | 7/1964 |
| GB | 1333475 | | | 10/1973 |
| GB | 1494915 | | | 12/1977 |
| GB | 2510042 | A | * | 11/2013 |
| WO | 9101295 | A1 | | 2/1991 |
| WO | 2005073358 | A1 | | 8/2005 |

OTHER PUBLICATIONS

O'Lenick, A.J. Jr. et al., "Amphoteric Surfactants—A Review of the Chemistry and Applications," HAPPI, Nov. 1986, pp. 70-74, and 125-126.

Ploog, U., "Aerosols Cosmetics Fragrances," Magazine for the Body Care Products Perfumery, and Aerosol-Industry, Jul. 1982, pp. 373-378.

EPO, International Search Report issued in International Application No. PC/EP2015/066172, dated May 10, 2016.

Kao: "Polyoxyethylene Glycerol fatty acid esters (cosmetics, Laundry and other use)", 1 page, retrieved from the Internet URL:https://chemical.kao.com/global/products/industry/c0104010202.

Wikipedia Article: "Cetostearyl alcohol", 1 page, retrieved from the Internet URL:https://en.wikipedia.org/wiki/Cetostearyl_alcohol.

Wikipedia Article: "Polyglycerol polyricinoleate", 2 pages, retrieved from the Internet URL:https://en.wikipedia.org/wiki/Polyglycerol_polyricinoleate.

Prospectors: "Dehymulse PGPH", Company: BASF.INCI, Name:Polyglyceryl-2 Dipolyhydroxystearate, 4 pages, retrieved from the Internet URL:https://www.ulprospector.com/en/eu/PersonalCare/Detail/804/31856/Dehymuls-PGPH.

CHEMIDplus: "Substance Name: PEG-30 glyceryl cocoate" RN: 68553-03-7, 1 page, retrieved from the Internet URL:https://chem.nlm.nih.gov/chemidplus/number/68553-03-7#names.

* cited by examiner

TRANSPARENT TEXTILE CARE AGENT

CROSS-REFERENCE TO RELATED APPLICATIONS

This application is a U.S. National-Stage entry under 35 U.S.C. § 371 based on International Application No. PCT/EP2015/066172, filed Jul. 15, 2015 which was published under PCT Article 21(2) and which claims priority to German Application No. 10 2014 010 875.9, filed Jul. 25, 2014, which are all hereby incorporated in their entirety by reference.

TECHNICAL FIELD

This disclosure relates to compositions, in particular textile care agents and fabric softener formulations that are optically clear and transparent and also have a viscous consistency, the use of these compositions as textile care agents and fabric softener formulations as well as a method for washing textile fabrics using these compositions, in particular textile care agents and fabric softener formulations. This disclosure likewise relates to methods for producing cationic compounds (EQ) as well as the resulting cationic compounds (EQ) and use thereof.

BACKGROUND

Ester quats (EQ), which are understood be quaternized fatty acid triethanolamine ester salts in general, are suitable to a great extent for both fiber finishing and hair finishing and have in the past years replaced a substantial portion of the conventional quaternary ammonium compounds such as the known distearyldimethylammonium chloride from the market due to the better ecotoxicological tolerability.

Although the known ester quats have very good properties with regard to the applications technology as well as a satisfactory biodegradability and a good skin cosmetic tolerability, the preparations containing ester quats that are known from the prior art have the disadvantage that they have turbidity. Special ester quats based on unsaturated fatty acids are present on the market and allow the production of optically clear formulations but high concentrations of these ester quats are required and solvents must be used to be able to prepare clear fabric softener formulations having the desired properties. This is another disadvantage in view of the cost of such formulations.

It is also desirable for such formulations to be viscous without having any thread-forming tendency to permit simple handling and dosing. Finally, there are also demands with regard to the stability of such formulations because not only is a uniform application-based quality required, but also a visually and olfactorily attractive structure of the product that will last the longest possible period of time are desired.

BRIEF SUMMARY

Liquid compositions, methods for producing cationic compounds, and methods for producing clear liquid compositions are provided herein. In an embodiment, a liquid composition includes water, at least one cationic compound (EQ), and at least one first emulsifier. The at least one cationic compound (EQ) is obtainable by reaction of (i) a mixture of at least one dicarboxylic acid of formula (I)

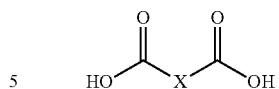

where X stands for a saturated or unsaturated hydrocarbon radical with 1 to 8 carbon atoms, and at least one monocarboxylic acid of formula (II)

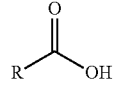

where R stands for a saturated or unsaturated hydrocarbon radical with 5 to 21 carbon atoms, with (ii) at least one tertiary amine of formula (III)

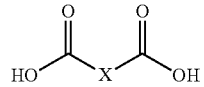

where R', R" and R''', independently of one another, stand for a ($C_2$ to C6) hydroxyalkyl group, with the resulting product reacted with (iii) at least one quaternizing agent for quaternization of at least one amino group contained in the reaction product of (i) and (ii). The at least one first emulsifier is a nonionic emulsifier with an HLB value of at least 12.0. The liquid composition has a pH (25° C.) between about 1 and 4.5.

In another embodiment, a method for producing a cationic compound (EQ) includes reacting (i) a mixture of at least one dicarboxylic acid of formula (I)

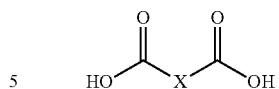

where X stands for a saturated or unsaturated hydrocarbon radical with 1 to 8 carbon atoms, and at least one monocarboxylic acid of formula (II)

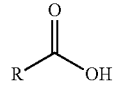

where R stands for a saturated or unsaturated hydrocarbon radical with 5 to 21 carbon atoms, with (ii) at least one tertiary amine of formula (III)

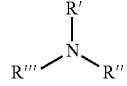

where R', R" and R'", independently of one another, stand for a ($C_2$ to $C_6$) hydroxyalkyl group, and then reacting the resulting product with (iii) at least one quaternizing agent for quaternization of at least one amino group contained in the reaction product of (i) and (ii).

In another embodiment, a method for producing clear liquid compositions includes producing an aqueous solution that includes at least one first emulsifier at a temperature above 35° C. The at least one first emulsifier is a nonionic emulsifier with an HLB value of at least 12.0. At least one cationic compound (EQ) is added to the aqueous solution. The at least one cationic compound (EQ) is obtainable by reaction of (i) a mixture of at least one dicarboxylic acid of formula (I)

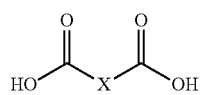

(I)

where X stands for a saturated or unsaturated hydrocarbon radical with 1 to 8 carbon atoms, and at least one monocarboxylic acid of formula (II)

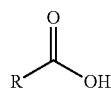

(II)

where R stands for a saturated or unsaturated hydrocarbon radical with 5 to 21 carbon atoms, with (ii) at least one tertiary amine of formula (III)

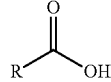

(II)

where R', R" and R'", independently of one another, stand for a ($C_2$ to $C_6$) hydroxyalkyl group, with the resulting product reacted with (iii) at least one quaternizing agent for quaternization of at least one amino group contained in the reaction product of (i) and (ii). The temperature of the at least one cationic compound (EQ) or a preparation containing the at least one cationic compound (EQ) is between 30° C. and 65° C. during the addition.

DETAILED DESCRIPTION

The following detailed description is merely exemplary in nature and is not intended to limit the hair treatment agents and methods for treating hair. Furthermore, there is no intention to be bound by any theory presented in the preceding background or the following detailed description.

This disclosure solves the problem of providing transparent viscous compositions containing ester quats but at least partially overcomes the disadvantages of known formulations as described above. The subject matter as contemplated herein is based on the surprising finding of the inventors that through the combination of special ester quats with certain nonionic emulsifiers, in particular in combination with thickeners, wherein cationic thickeners are preferred, it is possible to make available a viscous, optically clear and fragrant fabric softener formulation, which has a reduced concentration of softening substances in comparison with comparable market formulations at the same time and has a long stability in storage (no clouding, no unpleasant odor formation).

In a first aspect, this disclosure therefore relates to a liquid composition having a pH (25° C.) between about 1 and about 4.5, in particular between about 2 and about 3.5, comprising (a) water,
(b) at least on cationic compound (EQ) obtainable by reaction of
(i) a mixture of at least dicarboxylic acid of the formula (I)

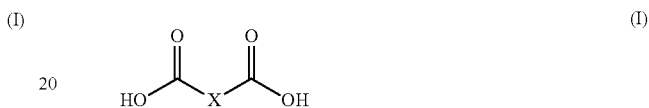

(I)

where X stands for a saturated or unsaturated hydrocarbon radical with 1 to 8 carbon atoms and at least one monocarboxylic acid of formula (II)

(II)

where R stands for a saturated or unsaturated hydrocarbon radical with 5 to 21 carbon atoms, with
(ii) at least one tertiary amine of formula (III)

(III)

where R', R" and R'" independently of one another stand for a $C_2$ to $C_6$ hydroxyalkyl group, in particular for 2-hydroxyethyl, and then reacting the resulting product with
(iii) at least one quaternizing agent for quaternization of at least one amino group contained in the reaction product and
(c) at least one first emulsifier, wherein the at least one first emulsifier is a nonionic emulsifier with an HLB value of at least about 12.0, in particular of at least about 13.0, preferably at least about 14.0, most preferably at least about 15.0.

The term "cationic compound (EQ)" means that the cationic compound is an ester quat.

The compositions are preferably textile care agents, in particular fabric softener formulations.

Another subject matter as contemplated herein is a method for treating textiles in which at least one textile is brought in contact with the liquid composition as contemplated herein.

Finally, another subject matter as contemplated herein is the use of the liquid composition as contemplated herein for care and/or conditioning of textile fabrics.

These and additional aspects, features and advantages as contemplated herein can be seen by those skilled in the art from a study of the following detailed description and claims. Each feature from an aspect of the present disclosure can be used in any other aspect of the present disclosure. Furthermore it is self-evident that the examples contained herein should describe and illustrate the various embodiments but should not restrict it and in particular the present disclosure is not restricted to these examples. Unless otherwise indicated, all percentage amounts are percent by weight. Numerical ranges given in the format "from x to y" include the values mentioned. If several preferred numerical ranges are specified in this format, it is self-evident that all ranges occurring due to the combination of the different end points are also detected. Furthermore, quantitative amounts relating to at least one component always denote the total amount of this type of component which is present in the composition unless something else is stated explicitly. This means that such quantitative amounts relate to the total amount of emulsifiers contained in the washing agent in conjunction with "at least one emulsifier," for example.

"At least one," as used herein, relates to 1 or more, for example 1, 2, 3, 4, 5, 6, 7, 8, 9 or more. In conjunction with components of the compositions described herein, this statement does not relate to the absolute amount of molecules but instead to the type of component. "At least one emulsifier" for example therefore denotes one or more different emulsifiers, i.e., one or more different types of emulsifiers. Together with quantitative statements of amount, these quantitative statements of amount are based on the total amount of the suitably designated type of component, as already defined above.

The term "HLB" (hydrophilic-lipophilic balance) which is used below defines the hydrophilic and lipophilic amounts of corresponding substance classes (emulsifiers here) in a value range from 1 to 20 according to the following formula (Griffin, Classification of surface active agents by HLB, J. Soc. Cosmet. 1 (5), 311-326, 1949; Griffin, Calculation of HLB values of non-ionic surfactants, J. Soc. Cosmet. Chem. 5 (4), 249-256, 1954):

$$HLB=20\times(1-(M_1/M))$$

where M=molecular weight of the entire molecule
and M1=molecular weight of the lipophilic component of the molecule.

Low HLB values (>1) describe lipophilic substances, while high HLB values (<20) describe hydrophilic substances. Thus for example foam suppressants typically have HLB values in the range of about 1.5 to about 3 and are insoluble in water. Emulsifiers for W/O emulsions typically have an HLB value in the range of about 3 to about 8, whereas emulsifiers for O/W emulsions typically have HLB values in the range of about 8-18. Wash-active substances typically have HLB values in the range of about 13-15 and solubilizers have values in the range of about 12-18.

The HLB value of an emulsifier mixture consisting of two nonionic emulsifiers can be calculated as follows:

HLBmixture=HLBemulsifier 1×amountemulsifier 1 in the total contentemulsifier 1+HLBemulsifier 2×amountemulsifier 2 of the total contentemulsifier This can be expanded with no problem to include mixtures with more than two nonionic emulsifiers.

The at least one nonionic emulsifier and the mixture of nonionic emulsifiers as contemplated herein preferably have an HLB value of about 12.0-19.5, in particular of about 13.0-19.5, preferably of about 14.0-19.5, especially preferably of about 15.0-19.5.

In some specific embodiments, the at least one nonionic emulsifier and the mixture of the nonionic emulsifiers as contemplated herein preferably have an HLB value of about 12.0-18.0, in particular of about 13.0-18.0, preferably of about 14.0-18.0, especially preferably of about 15.0-18.0.

In various specific embodiments, the at least one nonionic emulsifier and the mixture of the nonionic emulsifiers as contemplated herein preferably have an HLB value of about 12.0-17.0, in particular about 13.0-17.0, preferably of about 14.0-17.0, especially preferably of about 15.0-17.0.

If the composition has at least two or more nonionic emulsifiers, then the second and additional nonionic emulsifier(s) may have an HLB value which is below about 12.0, below about 13.0, below about 14.0 or below about 15.0, as long as the HLB value of the mixture of nonionic emulsifiers amounts to at least about 12.0, in particular at least about 13.0, preferably at least about 14.0, especially preferably at least about 15.0.

"Liquid," as used herein, includes all compositions that are flowable under standard conditions (20° C., 1013 mbar), including corresponding pastes and gels.

As indicated herein, the pH relates is based on the pH determined at 25° C. unless otherwise indicated explicitly. The pH is determined by means of Portamess 911X pH meter. The standard for determination of pH is DIN EN 1262.

It has surprisingly been discovered that at a pH of about 1.0 to about 4.5, in particular about 2.0 to about 3.5, the composition as contemplated herein is especially stable. The composition remains clearer than comparative compositions over long storage times, i.e., it has a lower NTU value by comparison, and a lower turbidity value. Likewise the odor remains more pleasant than that of comparable compositions. With respect to a pleasant odor, the standard here is an odor that is less intense or does not even smell of fatty acid. Without trying to be bound to a certain theory it is assumed that the hydrolysis of the ester quats is prevented by the pH according to the patent claim and it is thereby advantageously stabilized. The formation of free fatty acids by ester quat hydrolysis is avoided.

The amount of the at least one cationic compound (EQ) (b) defined above in the composition is preferably about 0.1 to about 30% by weight, especially about 2-10% by weight.

The cationic compounds used as contemplated herein are ester quats (EQ) and products of the reaction of the following reagents:
(i) a mixture of at least dicarboxylic acid of formula (I)

where X stands for a saturated or unsaturated hydrocarbon group with 1 to 8 carbon atoms and at least one monocarboxylic acid of the formula (II)

wherein R stands for a saturated or unsaturated hydrocarbon radical with 5 to 21 carbon atoms, with (ii) at least one tertiary amine (alkanolamine) of formula (III)

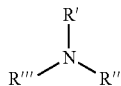

(III)

where R', R" and R'" independently of one another stand for a $C_2$ to $C_6$ hydroxyalkyl group, in particular for 2-hydroxyethyl,
and then reacting the resulting product with
(iii) at least one quaternizing agent for quaternization of at least one amino group contained in the reaction product.

Examples of dicarboxylic acids but may be considered in principle as starting materials in the sense of the present disclosure include those of formula (I) in which X stands for optionally hydroxy-substituted, linear or branched alkylene group with 1 to 8 carbon atoms. Typical examples include, without being limited to these, succinic acids, maleic acid, glutaric acid and in particular adipic acid. X preferably stands for ethane-1,2-diyl, propane-1,2-diyl, propane-1,3-diyl, butane-1,4-diyl, hexane-1,4-diyl or cyclohexane-1,4-diyl, especially preferably for butane-1,4-diyl. The dicarboxylic acid according to formula (II) is preferably adipic acid.

In a monocarboxylic acid of formula (II), RCO preferably stands for an aliphatic linear or branched acyl radical with 6 to 22 carbon atoms and 0 and/or 1, 2 or 3 double bonds. Typically examples include, without being limited to caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, eleostearic acid, arachic acid, gadoleic acid, behenic acid and erucic acid as well as their technical mixtures thereof which are obtained for example by pressure splitting of natural fats and oils, in the reduction of aldehydes from Roelen's oxosynthesis or dimerization of unsaturated fatty acids. Stearic acids, isostearic acids, palmitic acid, myristic acid, lauric acid, capric acid, caprylic acid, 2-ethylhexanoic acid, 2-octyldodecanoic acid, capric acid, oleic acid, linoleic acid, linolenic acid, partially hydrogenated coconut fatty acid, palm fatty acid, palm kernel fatty acid, tallow fatty acid and mixtures of two or more of the aforementioned acids. In general it is especially preferably for R in formula (II) to stand for a linear or branched C5 to C21 hydrocarbon radical with 0 to 3 double bonds. The monocarboxylic acid of formula (II) is preferably stearic acid.

Alkanolamines of formula (III) which may be considered as the central nitrogen compounds in the sense of the present disclosure contain a hydroxyalkane radical (alkanol radical) with 2 to 6 carbon atoms, preferably 2 to 4 carbon atoms. Triethanolamine is preferably used.

In a particularly preferred specific embodiment, the at least one cationic compound (EQ) (b) contains or consists of a compound of formula (K1):

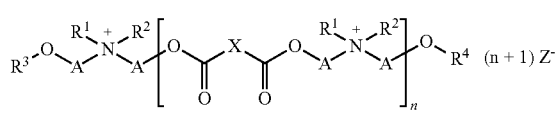

(K1)

In this formula X stands for a saturated or unsaturated hydrocarbon radical with 1 to 10 carbon atoms, in particular for butane-1,4-diyl, A stands for a (C2 to C6)-alkanediyl group, in particular for ethane-1,2-dyl, R1 stands for a (C2 to C4)-hydroxyalkyl group or a (C6 to C22)-acyloxy-(C2 to C4)-alkyl group, in particular for 2-hydroxyethyl or 2-((C6 to C22)-acyloxy)ethyl, R2 stands for methyl or ethyl, R3 and R4 independently of one another stand for a hydrogen atom or a (C6 to C22)-acyl group, n stands for 1 or 2 and Z– stands for any anion, in particular methyl sulfate, with the provision that according to formula (K1) at least one of the groups R1, R3 or R4 stands for a (C6 to C22)-acyl radical.

The ester quats that can be used as contemplated herein are ideally liquid to pasty at temperatures around 20° C.

The term "pasty" as used herein serves to describe the condition of a composition and means that the composition is not flowable at 20° C. and atmospheric pressure. Under an elevated pressure (>1 bar) and/or at 85° C. at least, the composition enters a state in which it is present as a flowable composition. Therefore it may be necessary in practice to melt the pasty composition, for example the contemplated ester quat, and incorporate it in the flowable condition into the composition as contemplated herein.

The agents as contemplated herein may contain the ester quats in amounts of about 2 to about 60, preferably about 2 to about 30% by weight—based on the total amount of the liquid composition—in the end product.

The monocarboxylic acids of formula (II) and the dicarboxylic acids of formula (I) can be used in a molar ratio of about 1:10 to about 10:1. However, it has proven advantageous to adjust a molar ratio of about 1:1 to about 4:1 and in particular about 1.5:1 to about 3:1. The trialkanolamines (III) on the one hand and the acids—i.e., monocarboxylic acids (II) and dicarboxylic acids (I) together—may be used in a molar ratio of about 1:1.2 to about 1:2.4. A molar ratio of trialkanolamine:acids from about 1:1.5 to about 1:1.8 has proven optimal.

Synthesis processes for supplying the ester quats used as contemplated herein are known from the prior art in general. In particular the esterification can be carried out in a known way as described in international patent application WO 91/01295. The esterification is advantageously carried out at temperature of about 120° C. to about 220° C. and in particular of about 130° C. to about 170° C. and pressures of about 0.01 to about 1 bar. Suitable catalysts that can be used include hypophosphorous acids and/or their alkali salts, preferably sodium hypophosphite which may be used in amounts of about 0.01 to about 0.1 and preferably about 0.05 to about 0.07% by weight, based on the starting materials. From the standpoint of a particularly high color quality and stability, concurrent use of alkali and/or alkaline earth borohydrides such as potassium, magnesium and in particular sodium borohydride has proven advantageous. The cocatalysts are usually used in amounts of about 50 to about 1000 and in particular about 100 to about 500 ppm—again based on the starting materials. Corresponding processes are also the subject matter of the two German patent specifications DE 4308792 C1 and DE 4409322 C1, to the teachings of which reference is herewith made explicitly. It is possible to use mixtures of monocarboxylic acids and dicarboxylic acids in esterification, but to carry out the esterification with the two component one after the other.

To synthesis ester quats containing polyalkylene oxide, the ester can be alkoxylated before quaternization. This may take place in a known way, i.e., in the presence of basic catalysts and at elevated temperatures. Examples of suitable catalysts include alkali and alkaline earth hydroxides and alcoholates, preferably sodium hydroxide and in particular sodium methanolate. The amount used is usually about 0.5 to about 5 and preferably about 1 to about 3% by weight, based on the starting materials. When using these catalysts, primarily free hydroxyl groups are alkoxylated. However if calcined hydrotalcites or hydrotalcites that have been hydrophobized with fatty acids are used as the catalysts, the result is insertion of the alkylene oxides into the ester bonds. Suitable alkylene oxides for use here include ethylene and propylene oxide as well as mixtures thereof (random or block distribution). A reaction is usually carried out at temperatures in the range of about 100° C. to about 180° C. By incorporating an average of 1 to 10 mol alkylene oxide per mol ester, the hydrophilicity of the ester quats is increased, the solubility is improved and the reactivity to anionic surfactants is reduced.

Quaternization of monocarboxylic acid/dicarboxylic acid trialkanolamine esters may be carried out in essentially known ways. Although the reaction with the alkylating agents can also be carried out in the absence of solvents, it is advisable to also use at least small amounts of water or lower alcohols, preferably isopropyl alcohol, to produce concentrates having a solids content of at least about 80 and in particular at least about 90% by weight.

Suitable alkylating agents include alkyl halides, such as, for example, methyl chloride, dialkyl sulfate, such as, for example, dimethyl sulfate or diethyl sulfate or dialkyl carbonates, such as, for example, dimethyl carbonate or diethyl carbonate. The esters and alkylating agents are generally used in a molar ratio of about 1:0.95 to about 1:1.05, i.e., approximately a stoichiometric ratio. The reaction temperature is usually about 40° C. to about 80° C. and in particular about 50° C. to about 60° C. Following the reaction it is advisable to destroy any unreacted alkylating agent by adding for example ammonia, an (alkanol)amine, an amino acid or an oligopeptide, as described in the German patent application DE 4026184 A1 for example.

In preferred embodiments, the quaternizing agent is dimethyl sulfate.

The term "polymer" or "copolymer" as used herein includes polymers of at least 21 monomer units, more preferably at least about 35 monomer units, even more preferably at least about 45 monomer units and most preferably at least about 50 monomer units. In the case of copolymers, the polymer as defined above includes at least two different monomer units.

The term "oligomer" as used herein includes molecules of two up to and including 20 monomer units.

A "monomer" is a structural unit of an oligomer or a polymer/copolymer.

As contemplated herein the ester quats described above are combined with at least one nonionic emulsifier with an HLB value of at least about 12.0, in particular of at least about 13.0, preferably of at least about 14.0 and most preferably of at least about 15.0. In special embodiments, the ester quats described above are combined with at least one nonionic emulsifier having an HLB value of at least about 14.0, most preferably of at least about 15.0. The following nonionic emulsifiers may be considered in particular as the nonionic emulsifiers for the contemplated formulations:

Addition products of 2 to about 50 mol ethylene oxide and/or 0 to about 5 mol propylene oxide onto linear fatty alcohols with 8 to 22 carbon atoms, onto fatty acids with 8 to 22 carbon atoms, onto alkyl phenols with 8 to 15 carbon atoms in the alkyl group and alkylamine with 8 to 22 carbon atoms in the alkyl radicals; alkyl and/or alkenyl oligoglycosides with 8 to 22 carbon atoms in the alk(en)yl radical and their ethoxylated analogs;

Addition products of 1 to about 15 mol ethylene oxide onto castor oil and/or hydrogenated castor oil;

Addition products of about 15 to about 60 mol ethylene oxide onto castor oil and/or hydrogenated castor oil; partial esters of glycerol and/or sorbitan with unsaturated, linear or saturated branched fatty acids with 12 to 22 carbon atoms and/or hydroxycarboxylic acids with 3 to 18 carbon atoms as well as their adducts with 1 to 30 mol ethylene oxide; partial esters of polyglycerol (average degree of self-condensation 2 to 8), polyethylene glycol (molecular weight about 200 to about 5000), trimethylolpropane, pentaerythritol, sugar alcohols (e.g., sorbitol), alkyl glucosides (e.g., methyl glucoside, butyl glucoside, lauryl glucoside) and polyglucosides (e.g., cellulose) with saturated and/or unsaturated, linear or branched fatty acids with 12 to 22 carbon atoms and/or hydroxycarboxylic acids with 3 to 18 carbon atoms as well as their adducts with 1 to about 30 mol ethylene oxide;

Mixed esters of pentaerythritol, fatty acids, citric acid and fatty alcohol according to DE 1165574 PS and/or mixed esters of fatty acids with 6 to 22 carbon atoms, methyl glucose and polyols, preferably glycerol or polyglycerol;

Mono-, di- and trialkyl phosphates as well as mono-, di- and/or tri-PEG-alkyl phosphates and salts thereof;

Lanolin alcohols;

Polysiloxane-polyalkyl-polyether copolymers and/or the corresponding derivatives as well as Polyalkylene glycols.

The addition products of ethylene oxide and/or propylene oxide onto fatty alcohols, fatty acids, alkyl phenols or castor oil are known products that are available commercially. These are homolog mixtures whose average degree of alkoxylation corresponds to the ratio of the substance quantities of ethylene oxide and/or propylene oxide and substrate with which the addition reaction is carried out. C12/18 fatty acid mono- and diesters of the addition products of ethylene oxide onto glycerol are known from DE 2024051 PS as a remoisturizing agent for cosmetic preparations.

Alkyl and alkenyl oligoglycosides, their synthesis and use are known from the prior art. They are synthesized in particular by reacting glucose or oligosaccharides with primary alcohols having 8 to 18 carbon atoms. With respect to the glycoside radical it is true that both monoglycosides in which a cyclic sugar radical is glycosidically bonded to the fatty alcohol as well as oligomeric glycosides with a degree of oligomerization of up to preferably approx. 8 are also suitable. The degree of oligomerization is a statistical average which is not based on a usual homolog distribution for such technical products.

Typical examples of suitable partial glycerides include hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride as well as the technical grade mixtures which may still contain small amounts of triglyceride as a minor contaminant from the synthesis process. Also suitable are addition products of 1 to about 30 preferably about 5 to about 10 mol ethylene oxide onto the aforementioned partial glycerides.

Suitable sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate as well as the technical grade mixtures thereof. Also suitable are addition products of 1 to about 30 preferably about 5 to about 10 mol ethylene oxide onto the aforementioned sorbitan esters.

Typical examples of suitable polyglycerol esters include polyglycerol-2 dipolyhydroxystearate (Dehymuls® PGPH), polyglycerol-3-diisostearate (Lameform® polyglycerol-4 isostearate (Isolan® GI 34), polyglyceryl-3 oleate, diisostearoyl polyglyceryl-3 diisostearate (Isolan® PDI), polyglycerol-3 methyl glucose distearate (Tego Care® 450), polyglyceryl-3 beeswax (Cera Bellina®), polyglyceryl-4 caprate (polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate as well as mixtures thereof.

Examples of other polyol esters include the mono-, di- and triesters of trimethylol propane or pentaerythritol with lauric acid, coco fatty acid, tallow fatty acid, palmitic acid, stearic acid, oleic acid, behenic acid and the like, optionally reacted with 1 to about 30 mol ethylene oxide.

Especially preferred addition products as contemplated herein are those of about 15 to about 60 mol ethylene oxide, in particular about 40 to about 60 mol ethylene oxide, onto castor oil and/or hydrogenated castor oil, preferably with an HLB value of at least about 14.0, more preferably at least about 15.0.

Fundamentally, it is true that higher concentrations of nonionic emulsifier in the compositions interfere with turbidity.

Preferred nonionic emulsifiers include Eumulgin CO 40, Eumulgin CO 60, Emulan ELH 60, Eumulgin 410, Eumulgin 455, Emulan 40 and Emulan EL (all from BASF). These castor oil-based emulsifiers are advantageous in the storage test in comparison with other nonionic emulsifiers for example Dehydol LT7. Eumulgin CO 40, Eumulgin CO 60 and Emulan ELH 60 here lead to particularly advantageous compositions which have NTU values of 30 or less for 24 weeks in the summer, fall and winter program (see example). These compositions thus remain clear for a long period of time and over a wide temperature interval.

The agents as contemplated herein may contain the nonionic emulsifiers in amounts of about 0.1 to about 50, preferably about 1 to about 30 and in particular about 2 to about 10% by weight, based on the final concentration.

The composition as contemplated herein, which is selected from the nonionic emulsifiers defined in this patent application and includes at least one, preferably at least two ethylene oxide groups, is especially preferred.

This means that in certain embodiments of the at least one emulsifier and all other nonionic emulsifiers are selected from the group of nonionic emulsifiers, which have at least one, preferably at least two ethylene oxide groups. The at least one first nonionic emulsifier must have an HLB value of at least about 12.0, in particular at least about 13.0, preferably at least about 14.0, most preferably at least about 15.0. If the composition has two or more nonionic emulsifiers, then all of them have at least one, preferably at least two ethylene oxide groups.

In addition to at least one nonionic emulsifier, the compositions as contemplated herein, in particular the fabric softener formulations may also contain additional emulsifiers, for example cationic and/or anionic emulsifiers.

In some embodiments, the composition as contemplated herein does not contain a cationic emulsifier.

In various preferred embodiments, the composition as contemplated herein does not contain any anionic emulsifier.

The composition as contemplated herein preferably does not contain any cationic emulsifier or any anionic emulsifier.

In the compositions as contemplated herein, the at least one nonionic emulsifier and the at least one ester quat are present in a weight ratio of at least about 0.5:1, preferably at least about 0.65:1, more preferably at least about 1:1, even more preferably at least about 2:1.

The known cationic emulsifiers include fatty acid amidoamines and/or the quaternization products thereof:

Fatty acid amidoamines that may be considered as cationic emulsifiers include the condensation products of fatty acids with optionally ethoxylated di- or oligoamines which preferably follow the formula (IV):

$$R^1CO\text{—}NR^2\text{-}[(A)\text{-}NR^3]_n\text{—}R^4 \quad (IV)$$

in which $R^1CO$ stands for a linear or branched, saturated or unsaturated acyl radical with 6 to 22 carbon atoms, $R^2$ stands for hydrogen or an optionally hydroxy-substituted alkyl radical with 1 to 4 carbon atoms, $R^3$ and $R^4$ independently of one another stand for hydrogen, a $(CH_2CH_2O)_mH$— group or an optionally hydroxy-substituted alkyl group with 1 to 4 carbon atoms, A stands for a linear or branched alkylene group with 1 to 6 carbon atoms, n stands for numbers from 1 to 4 and m stands for numbers from 1 to about 30. Typical examples include the condensation products of caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, eleostearic acid, arachic acid, gadoleic acid, behenic acid and erucic acid as well as their technical mixtures with ethylenediamine, propylenediamine, diethylenetriamine, dipropylenetriamine, triethylenetetramine, tripropylenetetramine as well as their adducts with 1 to 30 preferably 5 to 15 and in particular 8 to 12 mol ethylene oxide. The use of ethoxylated fatty acid amidoamines is preferred because in this way the hydrophilicity of the emulsifiers can be adjusted accurately to that of the active ingredients to be emulsified. Instead of the fatty acid amidoamines, their quaternization products which are obtained by reacting the amidoamines with suitable alkylating agents, such as, for example, methyl chloride or in particular dimethyl sulfate according to known methods, may also be used. The quaternization products preferably follow from formula (V):

$$[R^1CO\text{—}NR^2\text{-}[(A)\text{-}N^+(R^3R^6)]_n\text{—}R^4]X \quad (V)$$

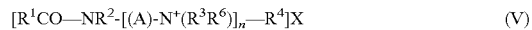

where $R^1CO$ stands for a linear or branched, saturated or unsaturated acyl radical with 6 to 22 carbon atoms, $R^2$ stands for hydrogen or an optionally hydroxy-substituted alkyl radical with 1 to 4 carbon atoms, $R^3$ stands for hydrogen, a ($CH_2CH_2O)_mH$— group or an optionally hydroxy-substituted alkyl radical with 1 to 4 carbon atoms, $R^4$ stands for $R^1CO$, hydrogen, a ($CH_2CH_2O)_mH$— group or an optionally hydroxy-substituted alkyl radical with 1 to 4 carbon atoms, $R^6$ stands for an alkyl radical with 1 to 4 carbon atoms, A stands for a linear or branched alkylene group with 1 to 6 carbon atoms, n stands for numbers from 1 to 4, m stands for numbers from 1 to 30 and X stands for halide, specifically chloride or alkyl sulfate, preferably methyl sulfate. For example, the methylation products of the fatty acid amidoamines already mentioned above as preferred are suitable for this purpose. In addition, mixtures of fatty acid amidoamines and their quaternization products, which can be produced especially easily by performing the quaternization only up to a certain degree instead of performing complete quaternization, may also be used.

The compositions as contemplated herein may contain the fatty acid amidoamines and/or their quaternization products in amounts of about 0.1 to about 50%, preferably about 1 to about 30% and in particular about 2 to about 10% by weight, based on the final concentration.

The known anionic emulsifiers include betaines.

Betaines that may be used as the anionic emulsifiers include known surfactants which are synthesized primarily by carboxyalkylation, preferably carboxymethylation of aminic compounds. The starting materials are preferably condensed with halocarboxylic acids or the salts thereof, in particular with sodium chloroacetate, wherein 1 mol of salt is formed per mol of betaine. Furthermore the addition of unsaturated carboxylic acids, such as, for example, acrylic acid is also possible. Regarding the nomenclature and in particular the differentiation between betaines and "true" amphoteric surfactants, reference should be made to the contribution by U. Ploog in Seifen-Öle-Fette-Wachse, 108, 373 (1982). Additional reviews of this topic can be found for example by A. O'Lennick et al. in HAPPI, November 70 (1986), S. Holzman et al. in Tens. Surf. Det. 23, 309 (1986), R. Bibo et al. in Soap Cosm. Chem. Spec., April 46 (1990) and P. Ellis et al. in Euro. Cosm. 1, 14 (1994). Examples of suitable betaines include the carboxyalkylation products of secondary and in particular tertiary amines following formula (VI):

R7-N(R8R9)-(CH2)pCOOA    (VI)

where R7 stands for alkyl and alkenyl radicals with 6 to 22 carbon atoms, R8 stands for hydrogen or alkyl radicals with 1 to 4 carbon atoms, R9 stands for alkyl radicals with 1 to 4 carbon atoms, p stands for numbers from 1 to 6, and A stands for alkali and/or alkaline earth metal or ammonium. Typical examples include the carboxymethylation products of hexyl methylamine, hexyl dimethylamine, octyl dimethylamine, decyl dimethylamine, dodecyl methylamine, dodecyl dimethylamine, dodecylethyl methylamine, C12/14 cocoalkyl dimethylamine, myristyl dimethylamine, cetyl dimethylamine, stearyl dimethylamine, stearylethyl methylamine, oleyl dimethylamine, C16/18 tallow alkyl dimethylamine as well as their technical grade mixtures.

In addition, carboxyalkylation products of amidoamines that conform to formula (VII) may also be used:

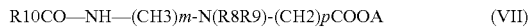

R10CO—NH—(CH3)m-N(R8R9)-(CH2)pCOOA    (VII)

where R10CO stands for an aliphatic acyl radical having 6 to 22 carbon atoms and 0 or 1 to 3 double bonds, m stands for a numbers from 1 to 3 and R3, R9, p and A have the meanings given above. Typical examples include the reaction products of fatty acids having 6 to 22 carbon atoms namely caproic acid, caprylic acid, capric acid, lauric acid, myristic acid, palmitic acid, palmoleic acid, stearic acid, isostearic acid, oleic acid, elaidic acid, petroselinic acid, linoleic acid, linolenic acid, elaeostearic acid, arachic acid, gadoleic acid, behenic acid and erucic acid as well as their technical grade mixtures with N,N-dimethylaminoethylamine, N,N-dimethylaminopropylamine, N,N-diethylaminoethylamine and N,N-diethylaminopropylamine which are condensed with sodium chloroacetate. Use of a condensation product of C8/18 coconut fatty acid-N,N-dimethylamino-propylamide with sodium chloroacetate is preferred.

In addition, imidazolines that conform to formula (VIII) may also be considered as suitable starting materials:

(VIII)

where R5 stands for an alkyl radical having 5 to 21 carbon atoms, R6 stands for a hydroxyl group, an OCOR5 or NHCOR5 radical and m stands for 2 or 3. These substances are also known substances which can be obtained, for example, by cyclizing condensation of 1 or 2 mol fatty acid with polyvalent amines, such as, for example, aminoethylethanolamine (AEEA) or diethylene triamine. The corresponding carboxyalkylation products are mixtures of various open-chain betaines. Typical examples include the condensation products of the aforementioned fatty acids with AEEA, preferably with imidazolines based on lauric acid or again C12/14 coconut fatty acid, which are then betainized with sodium chloroacetate.

The compositions as contemplated herein may contain the betaines in amounts of about 0.1 to about 50%, preferably about 1 to about 30% and in particular about 2 to about 10% by weight, based on the final concentration.

Combinations of nonionic emulsifiers with additional nonionic emulsifiers may be present in the compositions as contemplated herein wherein the HLB value of the emulsifier mixture of the (at least one) first and (at least one) second nonionic emulsifier(s) is at least about 12.0, in particular at least about 13.0, preferably at least about 14.0, most preferably at least about 15.0. The ratio of the first emulsifier to the second emulsifier is preferably about 0.9-0.1 to about 0.9-0.1. In a particularly preferred embodiment, the second emulsifier is also a nonionic emulsifier.

In a preferred embodiment, the compositions as contemplated herein may also contain a thickener, selected in particular from neutral thickeners, cationic thickeners and mixtures thereof.

The amount of thickener in the composition may be about 0.1-10% by weight, preferably about 0.5-5% by weight.

The thickeners that are suitable in general include, for example, grades of aerosil (hydrophilic silicic acids), polysaccharides, in particular xanthan gum, guar gum, agar, alginates and tyloses, carboxymethyl cellulose and hydroxyethyl cellulose, also higher molecular polyethylene glycol mono- and diesters of fatty acids, polyacrylates (e.g., Carbopole® from Goodrich or Synthalene® from Signa), polyacrylamides, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates with a narrow homolog distribution or alkyl oligoglucosides as well as electrolytes such as NaCl and ammonium chloride.

Suitable cationic thickener polymers include, for example, cationic cellulose derivatives, such as, for example, a quaternized hydroxyethyl cellulose, which is available under the designation Polymer JR 400® from Amerchol, cationic starch, copolymers of diallylammonium salts and acrylamides, quaternized vinyl pyrrolidone/vinyl imidazole polymers such as Luviquat® (BASF), condensation products of polyglycols and amines, quaternized collagen polypeptides, such as, for example, lauryl dimonium, hydroxypropyl hydrolyzed collagen (Lamequat® L/Grunau), quaternized wheat polypeptides, polyethyleneimine, cationic silicone polymers, such as, for example, amidomethicone, copolymers of adipic acid and dimethylaminohydroxypropyl diethylene triamine (Cartaretine®, Sandoz), copolymers of acrylic acid with dimethyldiallylammonium chloride (Merquat® 550, Chemviron), polyaminopolyamides, such as, for example, those described in FR 2252840 A as well as their crosslinked water-soluble polymers, cationic chitin derivatives, such as, for example, quaternized chitosan, optionally in microcrystalline distribution, condensation products of dihaloalkylenes, such as, for example, dibromobutane with bisdialkylamines, such as, for example, bisdimethylamino-1,3-propane, cationic guar gum, such as, for example, Jaguar® CBS, Jaguar® C-17, Jaguar® C-16 from the Celanese company, quaternized ammonium salt polymers, such as, for example, Mirapol® A-15, Mirapol® AD-1, Mirapol® AZ-1 from the company Miranol.

For the sake of thoroughness, anionic, zwitterionic, amphoteric and nonionic thickener polymers should also be mentioned in this context, for example, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and esters thereof, uncrosslinked and polyol-crosslinked polyacrylic acids, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinyl pyrrolidone/vinyl acetate copolymers, vinyl pyrrolidone/dimethylaminoethyl methacrylate/vinyl caprolactam terpolymers as well as optionally derivatized cellulose ethers and silicones.

In various embodiments, the compositions contain at least one nonionic thickener. Nonionic thickeners that are preferably used in the liquid compositions as contemplated herein are selected in particular from hydroxyethyl cellulose (HEC), hydroxypropyl cellulose (HPC), hydroxypropylmethyl cellulose (HPMC) and methyl cellulose (MC), guar, guar derivatives and mixtures of the aforementioned nonionic thickeners. For example, the nonionic thickener may be the 2-hydroxypropyl ether guar derivative Jaguar HP-105 from Rhodia.

In other preferred embodiments, the compositions contain at least one cationic thickener for example alternatively or in addition to the nonionic thickeners described above. In preferred embodiments, the cationic thickener comprises at least one copolymer of at least one monomer of the formula (M1) and at least one monomer of the formula (M2):

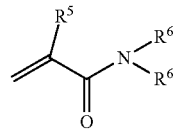 (M1)

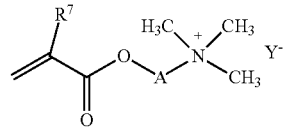 (M2)

where R5, R6 and R7, independently of one another, stand for hydrogen or a methyl group, A stands for ethane-1,2-diyl or propane-1,3-diyl, and Y− stands for any anion. The cationic thickener may also consist of the aforementioned copolymer. In certain embodiments, the liquid composition is characterized in that R6 according to formula (M1) stands for a hydrogen atom and/or R5 according to formula (M1) stands for a hydrogen atom and/or A according to formula (M2) stands for ethane-1,2-diyl or propane-1,3-diyl. In various embodiments, Y− stands for an anion selected from the group consisting of chloride and sulfate, in particular methyl sulfate.

It is preferable for said cationic thickener copolymer to be made up of about 95 to about 100% by weight of the monomers of formula (M1) and (M2), based on the total weight of the polymer.

In addition, the cationic thickener copolymer is present in a covalently crosslinked form in preferred embodiments. This covalent crosslinking is created by using at least one copolymerizable crosslinking agent. Suitable copolymerizable crosslinking agents have at least two ethylenically unsaturated groups and are selected for example from divinyl benzene, tetraallylammonium chloride, allyl acrylate, allyl methacrylate, diacrylate compounds of glycols, diacrylate compounds of polyglycols, dimethacrylate compounds of glycols, dimethacrylate compounds of polyglycols, butadiene, 1,7-octadiene, allylacrylamide, allylmethacrylamide, bis-acrylamidoacetic acid, N,N'-methylene-bis-acrylamide, polyol polyallyl ether and mixtures of two or more of these compounds.

The cationic thickener copolymer can be obtained by emulsion polymerization, for example. In preferred embodiments, it is present in the form of beads, wherein said beads preferably have an average particle diameter of about 10 µm to about 1000 µm, in particular of about 50 µm to about 1000 µm.

The cationic thickener copolymer is preferably present in a total amount of about 0.05 to about 2.0% by weight, in particular from about 0.1 to about 1.0% by weight, in the liquid compositions as contemplated herein.

In a few embodiments, the cationic thickener copolymer has a structure according to formula (M3):

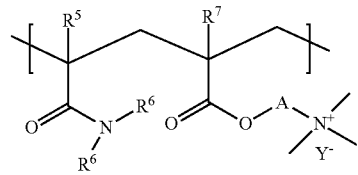 (M3)

where $R^5$, $R^6$ and $R^7$ independently of one another stand for a hydrogen atom or a methyl group, A stands for ethane-1, 2-diyl or propane-1,3-diyl, $Y^-$ stands for an anion. In various embodiments, $Y^-$ stands for an anion selected from the group consisting of chloride and sulfate, in particular, methyl sulfate. The cationic thickener copolymer is preferably Rheovis CSP from BASF.

Solvents that may be used in the agents as contemplated herein originate for example from the group of monovalent or polyvalent alcohols. Alkanolamines or glycol ethers may also be considered if they are miscible with water in the stated concentration range. The solvents are preferably selected from ethanol, n-propanol or isopropanol, butanols, glycol, propane or butanediol, glycerol, diglycol, propyl or butyl diglycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol methyl or ethyl ether, methoxy, ethoxy or butoxy triglycol, 1-butoxyethoxy-2-propanol, 3-methyl-3-methoxybutanol, propylene glycol t-butyl ether, water as well as mixtures of these solvents. In preferred embodiments, the solvent used in the liquid compositions is water.

In various embodiments, the liquid composition has a viscosity of about 100-300 mPas (20° C.). The measurement is performed using a Brookfield viscometer RV DV-II at 20 rpm and spindle 2.

According to various embodiments, the composition as contemplated herein according to this approach has an NTU value of 30 or less, wherein the determination is performed at 20° C. as explained in example 4. In various embodiments, the compositions still have an NTU value of about 30 or less after storage for 16 weeks at 40° C.

In addition to the ester quats, thickeners and emulsifiers combined as contemplated herein, the agents as contemplated herein may also contain additional ingredients that further improve the technical application properties and/or aesthetic properties of the composition, depending on the intended purpose, for example, as textile care agents or as fabric softeners. Within the scope as contemplated herein, preferred compositions contain, in addition to ester quats, emulsifiers and optional thickeners, one or more substances from the group of electrolytes, pH adjusting agents, scents, perfume carriers, fluorescent agents, dyes, hydrotropes, foam inhibitors, antiredeposition agents, enzymes, optical brighteners, graying inhibitors [antiredeposition agents], dye transfer preventers, anti-crease agents, dye transfer inhibitors, wetting improving agents, antimicrobial active ingredients, germicides, fungicides, antioxidants, corrosion inhibitors, antistatics, ironing aids, phobicizing and impregnating agents, swelling and antislip agents as well as UV absorbers.

Suitable electrolytes from the group of inorganic salts may include a large number of a wide range of salts. Preferred cations include the alkali metals and alkaline earth metals, preferred anions including the halides and sulfates. From the standpoint of synthesis, the use of NaCl or MgCl2 in the agents as contemplated herein is preferred.

The use of pH adjusting agents may be indicated in order to bring the pH of the agents as contemplated herein into the desired range. All known acids and/or bases can be used here as long as their use is not prohibited for ecological reasons or for technical reasons associated with applications and/or for reasons of consumer protection. The amount of these adjusting agents preferably does not exceed 1% by weight of the total formulation.

Coloring agents and fragrances are added to the agents as contemplated herein to improve the aesthetic impression of the products and to make available to the consumer a visually and sensorially "typical and unmistakable" product in addition to the softness accomplishment. Suitable perfume oils and/or fragrances that may be used include individual fragrance compounds, for example, the synthetic products of the type of esters, ethers aldehydes, ketones, alcohols and hydrocarbons. Fragrance compound of the type of the esters include, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include for example benzyl ethyl ether; the aldehydes include for example the linear alkanols with 8 to 18 carbon atoms, citral, citronellal, citronellyloxyacetaldehyde, cyclamen aldehyde, hydroxycitronellal, lilial and bourgeonal; the ketones include for example the ionones, α-isomethylionone and methyl cedryl ketone; the alcohols include anethol, citronellol, eugenol, geraniol, linalool, phenyl ethyl alcohol and terpineol; the hydrocarbons include mainly the terpenes such as limonene and pinene. However, mixtures of different fragrances which together create an appealing scent note are preferred. Such perfume oils may also contain natural fragrance mixtures such as those accessible from plant sources, e.g., pine oil, citrus oil, jasmine oil, patchouli oil, rose oil or ylang-ylang oil. Also suitable are muscatel, sage oil, chamomile oil, clove oil, lemon balm oil, mint oil, cinnamon leaf oil, lime blossom oil, juniper berry oil, vetiver oil, olibanum oil, galbanum oil and labdanum oil as well as orange blossom oil, neroli oil, orange peel oil and sandalwood oil.

The coloring agent content is usually less than about 0.01% by weight, whereas scents may constitute up to about 2% by weight of the total formulation.

The scents can be incorporated directly into the agents as contemplated herein but it may also be advantageous to apply the scents to carriers which enhance the adhesion of the perfume to the laundry and ensure a slower release of the scent for long lasting scent of the textiles. Cyclodextrins, in which the cyclodextrin-perfume complexes can be additionally coated with other auxiliary substances, have proven to be suitable examples of such carrier materials.

It should be noted that the perfume oils to be incorporated into the liquid formulations as contemplated herein can be emulsified well in order to be able to ensure the desired clear transparent consistency of the formulation as contemplated herein.

The compositions as contemplated herein are advantageously in the form of clear liquid in comparison with the prior art because they are available over a wide temperature range and for a long time in storage. Furthermore, they have a substantially weaker odor of fatty acid or none at all in comparison with known compositions. The amount of perfume oil can therefore be reduced or perfumes oils can be entirely omitted. This is advantageous for sensitive textile care products because they are preferably formulated without perfume oils. The omission of perfume oils may also be advantageous for cost reasons and production reasons.

In certain embodiments the compositions contain 0% by weight perfume oil.

To improve the aesthetic impression of the agents as contemplated herein, they may be colored by using suitable coloring agents. Preferred coloring agents, the choice of which will not pose any problems for those skilled in the art, have a great stability in storage and are insensitive to the other ingredients of the agents and to light and do not have a pronounced substantivity with respect to textile fibers so as not to discolor them.

For example, soaps, paraffins or silicone oils, which may optionally be applied to carrier materials, may be considered as foam inhibitors that can be used in the agents as contemplated herein. Suitable antiredeposition agents which are also known as soil repellents, include for example nonionic cellulose ethers such as methyl cellulose and methyl hydroxypropyl cellulose with a methoxy group content of about 15% to about 30% by weight and a hydroxypropyl group content of about 1% to about 15% by weight, each based on the nonionic cellulose ethers as well as the polymers of phthalic acid and/or terephthalic acid known from the prior art and/or derivatives thereof, in particular polymers of ethylene terephthalates and/or polyethylene glycol terephthalates or anionically and/or nonionically modified derivatives thereof. Of these, the sulfonated derivatives of phthalic acid and terephthalic acid polymers are particularly preferred.

To improve the flow behavior, hydrotropes, such as, for example, ethanol, isopropyl alcohol or polyols may be used. Polyols that may be used here preferably have 2 to 15 carbon atoms and at least two hydroxyl groups. The polyols may also contain other functional groups, in particular amino groups and/or may be modified with nitrogen. Typical examples include:

Glycerol,

Alkylene glycols, such as, for example, ethylene glycol, diethylene glycol, propylene glycol, butylene glycol, hexylene glycol as well as polyethylene glycols with an average molecular weight of about 100 to about 1000 Dalton, Technical grade oligoglycine mixtures with a degree of self-condensation of about 1.5 to about 10 such as technical grade diglycine mixtures with a diglycine content of about 40 to about 50% by weight, Methylol compounds, such as in particular trimethylolethane, trimethylolpropane, trimethylolbutane, pentaerythritol and dipentaerythritol, Low alkyl glucosides, in particular those with 1 to 8 carbon atoms in the alkyl radical, such as, for example, methyl and butyl glucoside, Sugar alcohols with 5 to 12 carbon atoms, such as, for example, sorbitol or mannitol Sugars with 5 to 12 carbon atoms, such as, for example, glucose or sucrose, Amino sugars, such as, for example, glucamine, Dialcoholamines such as diethanolamine or 2-amino-1,3-propanediol.

Enzymes include in particular those from the classes of hydrolases such as proteases, esterases, lipases and/or lipolytic enzymes, amylases, cellulases and/or other glycosyl hydrolases and mixtures of the aforementioned enzymes. All these hydrolases contribute to removal of spots such as spots causes by protein, fat or starch and graying in the laundry. Cellulases and other glycosyl hydrolases may also contribute to color maintenance and to an increase in the softness of the textile by removing pilling and microfibrils. Oxireductases may also be used for bleaching and/or inhibiting dye transfer. Enzymatic active ingredients obtained from bacterial strains or fungi such as *Bacillus subtilis*, *bacillus licheniformis*, *Streptomyces griseus* and *Humicola insolens* are also especially suitable. Of special interest are proteases of the subtilisin type and in particular proteases obtained from *Bacillus lentus* are preferably also used. Enzyme mixtures from protease and amylase, for example, or protease and lipase and/or lipolytic enzymes or protease and cellulose or cellulase and lipase and/or lipolytic enzymes or from protease, amylase and lipase and/or lipolytic enzymes or protease, lipase and/or lipolytic enzymes and cellulase, in particular protease and/or lipase-containing mixtures and/or mixtures with lipolytic enzymes. Examples of such lipolytic enzymes include the known cutinases. Peroxidases or oxidases have in some cases also proven to be suitable. The suitable amylases include in particular α-amylases, isoamylases, pullulanases and pectinases. As cellulases, preferably cellobiohydrolases, endoglucanases and β-glucosidases, which are also known as cellobiases, and/or mixtures of these are preferably used. Since various types of cellulase differ through their CMCase and avicelase activities, the desired activities can be adjusted through targeted blending of the cellulases.

The enzymes are usually supplied as mixtures with preservatives and stabilizers. The amount of the enzyme mixture in the composition may be, for example, approx. 0.01 to 5% by weight, preferably 0.12 to approx. 2% by weight.

The inventors have surprisingly found that the compositions as contemplated herein stabilize enzymes particularly well. The acidic and cationic compositions ensure that the enzymes have a much higher activity even after 4 weeks of storage at 23° C. and 40° C. in comparison with known compositions. Cellulases are stabilized particularly well. Compositions as contemplated herein containing cellulases are therefore especially effective in preventing or delaying the onset of graying of laundry.

Optical brighteners (so-called "whiteners") may even be added to the agents as contemplated herein to eliminate graying and yellowing of the treated textiles. These substances are absorbed onto the fibers and cause a lightening and simulated bleaching effect by converting invisible ultraviolet radiation into visible longer wavelength light, wherein the ultraviolet light absorbed from sunlight is emitted as a faintly bluish fluorescence, which, together with the yellowish tone of the grayed and/or yellowed laundry, yields pure white. Suitable compounds originate for example from the substances classes of 4,4'-diamino-2,2'-stilbenedisulfonic acids (flavonic acids), 4,4'-distyrylbiphenyls, methyl umbelliferones, coumarins, dihydroquinolinones, 1,3-diarylpyrazolines, naphthalimides, benzoxazole, benzisoxazole and benzimidazole systems as well as the pyrene derivatives substituted by heterocycles. The optical brighteners are usually used in amounts between about 0.1 and about 0.3% by weight, based on the finished agent.

Graying inhibitors have the job of keeping the dirt dissolved off the fibers suspended in the wash bath and thereby preventing the redeposition of the dirt. Water-soluble colloids usually of an organic type are suitable for this purpose, for example, the water-soluble salts of polymeric carboxylic acids, glue, gelatin, salts of ether sulfonic acids of starch or of cellulose or salts of acidic sulfuric acid esters of cellulose or of starch. Water-soluble polyamides containing acid groups are also suitable for this purpose. In addition, soluble starch preparations and other starch products in addition to those mentioned above may also be used for example degraded starch, aldehyde starches, etc. Polyvinylpyrrolidone can also be used. However, it is preferable to use cellulose ethers such as carboxymethyl cellulose (Na salt), methyl cellulose, hydroxyalkyl cellulose and mixed ethers such as methyl hydroxyethyl cellulose, methyl hydroxypropyl cellulose, methyl carboxymethyl cellulose and mixtures thereof in amounts from about 0.1 to about 5% by weight, based on the agents.

Textile fabrics in particular those made of rayon, viscose staple fiber, cotton and blends thereof may have a tendency to wrinkle because the individual fibers are sensitive to bending, folding, pressing and squeezing across the direction of the fiber, so the agents as contemplated herein may contain synthetic antiwrinkle agents. These include for example synthetic products based on fatty acids, fatty acid esters, fatty acid amides, alkylol esters, alkylol amides or fatty alcohols, mostly reacted with ethylene oxide, or products based on lecithin or modified phosphoric acid esters.

For combating microorganisms, the agents as contemplated herein may contain antimicrobial active ingredients. A distinction is made here between bacteriostatics and bactericides, fungistatics and fungicides, etc. depending on the antimicrobial spectrum and the mechanism of action. Important substances from these groups include for example benzalkonium chlorides. Preferred compounds within the scope as contemplated herein include for example alkylaryl sulfonates, halophenols and phenol mercury acetate, but these compounds may also be omitted entirely with the agents as contemplated herein.

To prevent unwanted changes in the agents and/or the treated textiles due to exposure to oxygen and other oxidative processes, the agents may contain antioxidants. This class of compounds includes for example substituted phenols, hydroquinones, pyrocatechols and aromatic amines as well as organic sulfides, polysulfides, dithiocarbamates, phosphites and phosphonates.

Increased wearing comfort can result from the additional use of antistatics which are also added to the agents as contemplated herein. Antistatics increase the surface conductivity and thus permit an improved discharge of the charges that develop. External antistatics are usually substances having at least one hydrophilic molecular ligand and they form a more or less hygroscopic film on the surfaces. These antistatics, most of which are surfactants, can be divided into those that contain nitrogen (amines, amides, quaternary ammonium compounds), those that contain phosphorus (phosphoric acid esters) and antistatics that contain sulfur (alkyl sulfonates, alkyl sulfates). External antistatics are described in the patent applications FR 1,156,513, GB 873 214 and GB 839 407 for example. The lauryl (and/or stearyl) dimethylbenzylammonium chlorides disclosed here are suitable antistatics for textiles and/or as additives to washing agents, wherein a finishing effect is additionally achieved.

To improve the water absorption capacity, the rewettability of the treated textiles and to facilitate ironing of the treated textiles, silicone derivatives for example may be used in the agents as contemplated herein. These additionally improve the rinse-out behavior of the agents as contemplated herein through their firm inhibiting properties. Preferred silicone derivatives include for example polydialkyl or alkylarylsiloxanes in which the alkyl groups have 1 to 5 carbon atoms and are partially or entirely fluorinated. Preferred silicones include polydimethylsiloxanes which may optionally be derivatized and then have amino-functional bonds or are quaternized and/or have Si—OH, Si—H and/or Si—Cl bonds. The viscosities of the preferred silicones are in the range between about 100 and about 100,000 centistokes at 25° C., where the silicones may be used in amounts between about 0.05 and about 5% by weight, based on the total agent.

Finally the agents as contemplated herein may also contain UV absorbers which are absorbed onto the treated textiles and improve the light fastness of the fibers. Compounds having these desired properties are compounds that are effective for example due to radiationless deactivation and derivatives of benzophenone with substituents in position 2 and/or 4. In addition, substituted benzotriazoles, acrylates with a phenyl substitution in position 3 (cinnamic acid derivatives), salicylates optionally with cyano groups in position 2, organic Ni complexes as well as natural substances such as umbelliferone and the endogenous urocanoic acid are also suitable.

To obtain optimal properties pertaining to the technical applications and to protect the products from microbial infestation, it may be advantageous to add preservatives to the products. Microbial contamination of the fabric softener as contemplated herein can be prevented by using standard commercial preservatives.

The total amount of additives may be about 1 to about 50%, preferably about 5 to about 40% by weight, based on the end product.

The formulations described here can be produced by techniques with which those skilled in the art are familiar for producing textile care agents and fabric softeners. This may be accomplished by mixing the raw materials, optionally by using high-shear mixing equipment, for example.

Another subject matter as contemplated herein however is a method for producing the clear liquid compositions as contemplated herein comprising the steps:
a) Preparing an aqueous solution containing the at least one first emulsifier at a temperature above 35° C., preferably above 40° C. and most preferably above 45° C.,
b) Adding the contemplated at least one cationic compound (EQ) to the solution prepared in step a), wherein the temperature of the at least one cationic compound (EQ) or a preparation containing the at least one cationic compound (EQ) is between 30° C. and 65° C. at the time of addition, preferably between 35° C. and 60° C. and most preferably between 40° C. and 55° C.

If the liquid composition as contemplated herein contains at least one thickener, which is a preferred embodiment as contemplated herein, then the method for producing the contemplated clear liquid composition includes the steps:
a) Preparing an aqueous solution containing at least one thickener at a temperature above 40° C., preferably above 50° C. and most preferably above 55° C., and
b) Adding the contemplated at least one first emulsifier to the aqueous solution prepared in step a), wherein the at least one first emulsifier or the composition containing the at least one first emulsifier is preheated to a temperature above 30° C., preferably above 35° C. and most preferably above 40° C.,
c) Adding the at least one cationic compound (EQ) as contemplated herein to the solution prepared in step b), wherein the temperature of the at least one cationic compound (EQ) or a preparation containing the at least one cationic compound (EQ) is between 30° C. and 65° C. at the time of addition, preferably between 35° C. and 60° C., most preferably between 40° C. and 55° C.

The method as contemplated herein ensures that the liquid compositions as contemplated herein can be prepared in clear form. In particular the liquid compositions as contemplated herein can be prepared in clear form repeatedly and without purification of the equipment used in this process.

In a preferred embodiment of the method as contemplated herein, the aqueous solution in method step a) includes about 15 to about 70% by weight, preferably about 20 to about 60% by weight, more preferably about 25 to about 50% by weight and most preferably about 30 to about 45% by weight water, wherein the % by weight is based on the clear liquid composition.

In another preferred embodiment of the method as contemplated herein, the solution obtained in step b) of the method without thickener and in step c) of the method with thickener is cooled by adding about 30 to about 85% by weight, preferably about 40 to about 80% by weight, more preferably about 50 to about 75% by weight and most preferably about 55 to about 70% by weight water, wherein the percent by weight is based on the clear liquid composition, wherein the water has a temperature of 10° C. to 29° C.

In another preferred embodiment of the method as contemplated herein, the at least one thickener in method step a) of the method with thickener is selected from the group consisting of neutral thickeners, cationic thickeners and mixtures thereof, wherein cationic thickeners are especially preferred. The at least one thickener is used in the method as contemplated herein in an amount of about 0.1 to about 10% by weight, wherein the % by weight is based on the clear liquid composition.

The present disclosure also relates to methods for treating textiles. In such methods, at least one textile is brought into contact with a liquid composition as described herein. The use of liquid compositions such as those described herein for care and/or conditioning of textile fabrics is also included.

In another aspect, this disclosure relates to methods for producing cationic compounds (EQ), so-called ester quats as well as compounds produced by such methods and use therefore, in particular in compounds for care and conditioning of textile fabrics. These compositions are preferably liquid.

The methods for synthesis of the cationic compounds are also described in this document in conjunction with the compositions as contemplated herein. To this extent reference is made to this disclosure for the definition of the method for synthesis of the cationic compound (EQ).

The methods for synthesis of a cationic compound (EQ) are characterized by reaction of
(i) a mixture of at least one dicarboxylic acid of formula (I)

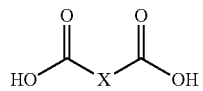

(I)

where X stands for a saturated or unsaturated hydrocarbon radical with 1 to 8 carbon atoms and at least one monocarboxylic acid of formula (II)

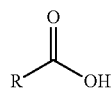

(II)

where R stands for a saturated or unsaturated hydrocarbon radical with 5 to 21 carbon atoms, with
(ii) at least one tertiary amine of formula (III)

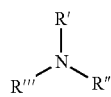

(III)

where R', R" and R''', independently of one another stand for a ($C_2$ to $C_6$) hydroxyalkyl group, in particular for 2-hydroxyethyl, and then reacting the resulting product with
(iii) at least one quaternizing agent for quaternization of at least one amino group contained in the reaction product.

In some embodiments the method for synthesis of the cationic compound is characterized in that the cationic compound (EQ) comprises a compound of formula (K1):

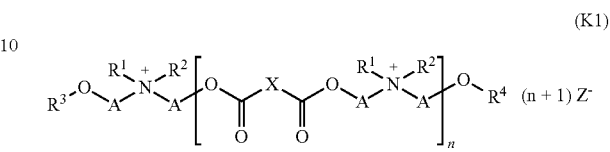

(K1)

where
X stands for a saturated or unsaturated hydrocarbon radical with 1 to 10 carbon atoms, in particular for butane-1,4-diyl,
A stands for a (C2 to C6) alkanediyl group, in particular for ethane-1,2-diyl,
R1 stands for a (C2 to C4) hydroxyalkyl group or a (C6 to C22) acyloxy-(C2 to C4) alkyl group, in particular for 2-hydroxyethyl or 2-((C6 to C22)acyloxy)ethyl,
R2 stands for methyl or ethyl,
R3 and R4 independently of one another stand for a hydrogen atom or a (C6 to C22) acyl group,
n stands for 1 or 2 and
Z– stands for an anion, in particular methyl sulfate,
with the provision that according to formula (K1) at least one of the groups R1, R3 or R4 includes a (C6 to C22) acyl radical.

In some embodiments of the method X in formula (I) stands for ethane-1,2-diyl, propane-1,2-diyl, propane-1,3-diyl, butane-1,4-diyl, hexane-1,4-diyl or cyclohexane-1,4-diyl, preferably for butane-1,4-diyl.

In various embodiments, R in formula (II) stands for a linear or branched C5 to C21 hydrocarbon radical with 0 to 3 double bonds.

In certain embodiments of the method, the resulting cationic compound (EQ) is liquid to pasty at 20° C.

In many embodiments of the method, succinic acid, maleic acid, glutaric acid, adipic acid or mixtures thereof are selected as the dicarboxylic acid of formula (I). Adipic acid is most especially preferred.

In some embodiments of the method, the monocarboxylic acid of formula (II) is stearic acid, isostearic acid, palmitic acid, myristic acid, lauric acid, capric acid, caprylic acid, 2-ethylhexanoic acid, 2-octyldodecanoic acid, capric acid, oleic acid, linoleic acid, linolenic acid, partially hydrogenated coconut fatty acid, palm fatty acid, palm kernel fatty acid, tallow fatty acid and mixtures of two or more of the aforementioned acids are selected. Stearic acid is most especially preferred.

In various embodiments of the method, the molar ratio of the monocarboxylic acids (II) to dicarboxylic acids (I) is in the range of 1:1 to 4:1, in particular in the range of 1.5:1 to 3:1, and the molar ratio of the alkanolamines (III) to the sum of mono- and dicarboxylic acids is in the range of 1:1.2 to 1:2.4, in particular preferably in the range of 1:1.5 to 1:1.8.

Dimethyl sulfate is preferably used as the quaternizing agent in this method.

In another aspect, this disclosure relates to cationic compounds (EQ) which are obtained by the methods described herein.

The methods as contemplated herein lead to cationic compounds which can be incorporated well into liquid compositions. These compositions are clear and have a pleasant scent for long periods of time and over wide temperature intervals. This is due in particular to the advantageous properties of the cationic compounds (EQ), which are obtained by the method as contemplated herein. To this extent, with regard to the advantages of the methods for synthesis of the cationic compound (EQ) and the resulting cationic compounds, reference is made to the advantages of the compositions as contemplated herein.

In another aspect, this disclosure relates to the use of a cationic compound (EQ) as described herein, in a composition, in particular a liquid composition, for care and/or conditioning of textile fabrics.

This disclosure contemplates the following points:

1. Liquid composition with a pH (25° C.) between about 1 and about 4.5, in particular between about 2 and about 3.5, comprising
    (a) water,
    (b) at least one cationic compound (EQ), obtainable by reaction of
    (i) a mixture of at least one dicarboxylic acid of the formula (I)

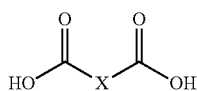

wherein X stands for a saturated or unsaturated hydrocarbon residue with 1 to 8 carbon atoms, and
    at least one monocarboxylic acid of the formula (II)

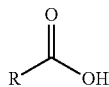

wherein R stands for a saturated or unsaturated hydrocarbon residue with 5 to 21 carbon atoms, with
    (ii) at least one tertiary amine of the formula (III)

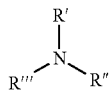

wherein R', R" and R''' independently of one another, stand for a ($C_2$ to $C_6$) hydroxyalkyl group, in particular for 2-hydroxyethyl,
    and then reacting the resulting product with
    (iii) at least one quaternizing agent for quaternization of at least one amino group contained in the reaction product, and
    (c) at least one first emulsifier, wherein the at least one first emulsifier is a nonionic emulsifier with an HLB value of at least about 12.0, in particular of at least about 13.0, preferably of at least about 14.0, most especially preferably of at least about 15.0.

2. The composition according to point 1, wherein
    (i) in the composition, the ratio of (c) to (b) amounts to at least about 0.5:1, preferably at least about 0.65:1, more especially at least about 1:1, even more especially at least about 2:1 and/or
    (ii) the amount of (b) in the composition is about 0.1-30% by weight, preferably about 2-10% by weight and/or
    (iii) the amount of (c) in the composition about 0.1-50% by weight, preferably about 1-30% by weight, in particular about 2-10% by weight,
    (iv) the composition comprises an enzyme mixture with an amount of about 0.01-5.0% by weight, based on the composition.

3. The composition according to point 1 or 2, wherein
    (a) the composition contains at least one second nonionic emulsifier, wherein the HLB value of the emulsifier mixture of the at least one first nonionic emulsifier and at least one second nonionic emulsifier is at least about 12.0, in particular at least about 13.0, preferably at least about 14.0, most especially preferably at least about 15.0, wherein preferably the ratio of the first nonionic emulsifier to the second nonionic emulsifier is about 0.9-0.1 to about 0.9-0.1 and/or
    (b) the at least one first nonionic emulsifier (c) is selected from the group consisting of addition products of about 15 to about 60 mol ethylene oxide, in particular about 40 to about 60 mol ethylene oxide, onto castor oil, hydrogenated castor oil and mixtures thereof, preferably with an HLB value of at least about 14.0, more preferably of at least about 15.0.

4. The composition according to any one of points 1-3, wherein the composition also contains at least one thickener, wherein the thickener is preferably present in an amount of about 0.1-10% by weight in the composition, wherein the thickener is selected from the group consisting of neutral thickeners, cationic thickeners and mixtures thereof.

5. The composition according to point 4, wherein the composition comprises at least one nonionic thickener, selected from the group consisting of hydroxyethylcellulose (HEC), hydroxypropylcellulose (HPC), hydroxypropylmethylcellulose (HPMC) and methylcellulose (MC), guar, guar derivates and mixtures of the aforementioned thickeners.

6. The composition according to point 4 or 5, wherein the composition comprises at least one cationic thickener, comprising at least one copolymer of at least one monomer of the formula (M1) and at least one monomer of the formula (M2)

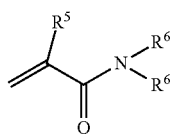

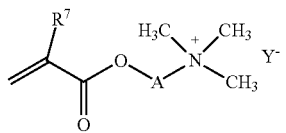

wherein $R^5$, $R^6$ and $R^7$, independently of one another, stand for a hydrogen atom or a methyl group,
    A stands for ethane-1,2-diyl or propane-1,3-diyl, $Y^-$ stands for an anion.

7. Liquid composition according to any one of points 1-6, characterized in that the at least one cationic compound (EQ) (b) contains a compound of the formula (K1),

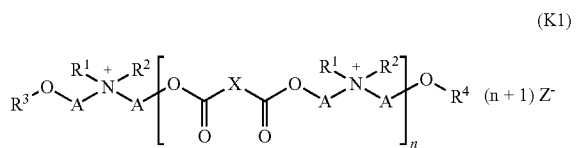

(K1)

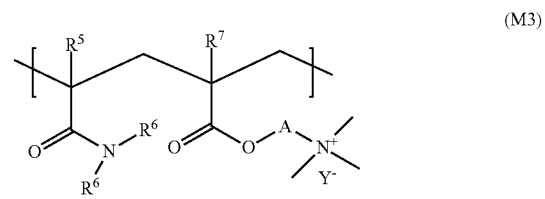

(M3)

wherein
X stands for a saturated or unsaturated hydrocarbon radical with 1 to 10 carbon atoms, in particular standing for butane-1,4-diyl,
A stands for a ($C_2$ to $C_6$)-alkanediyl group, in particular standing for ethane-1,2-diyl,
$R^1$ stands for a ($C_2$ to $C_4$)-hydroxyalkyl group or a ($C_6$ to $C_{22}$)-acyloxy-($C_2$ to $C_4$)-alkyl group, in particular standing for 2-hydroxyethyl or 2-(($C_6$ to $C_{22}$)-acyloxy) ethyl,
$R^2$ stands for methyl or ethyl,
$R^3$ and $R^4$, independently of one another, stand for a hydrogen atom or a ($C_6$ to $C_{22}$)-acyl group,
n stands for 1 or 2, and
$Z^-$ stands for an anion, in particular methyl sulfate,
with the provision that according to formula (K1), at least one of the groups $R^1$, $R^3$ or $R^4$ includes a ($C_6$ to $C_{22}$)-acyl radical.

8. Liquid composition according to point 6 or 7, characterized in that
(a) $R^6$ according to formula (M1) stands for a hydrogen atom; and/or
(b) $R^5$ according to formula (M1) stands for a hydrogen atom; and/or
(c) A according to formula (M2) stands for ethane-1,2-diyl or propane-1,3-diyl; and/or
(d) said cationic thickener copolymer is obtained from about 95% to about 100% by weight of the monomers of the formulas (M1) and (M2), based on the total weight of the polymer; and/or
(e) said cationic thickener copolymer is covalently cross-linked; and/or
(f) said cationic thickener copolymer is obtained by emulsion polymerization; and/or
(g) said cationic thickener copolymer is in the form of beads, wherein the beads are preferably present with an average particle diameter of about 10 μm to about 1000 μm, in particular of about 50 μm to about 1000 μm; and/or
(h) said cationic thickener copolymer is present in a total amount of 0.05 to 2.0% by weight, in particular of about 0.1 to about 1.0% by weight.

9. Liquid composition according to any one of points 6-8, characterized in that
(a) said cationic thickener copolymer is covalently cross-linked by using at least one copolymerizable crosslinking agent with at least two ethylenically unsaturated groups, in particular selected from divinylbenzene, tetraallylammonium chloride, allyl acrylate, allyl methacrylate, diacrylate compounds of glycols, diacrylate compounds of polyglycols, dimethacrylate compounds of glycols, dimethacrylate compounds of polyglycols, butadiene, 1,7-octadiene, allylacrylamide, allylmethycrylamide, bisacrylamidoacetic acid, N,N'-methylenebisacrylamide, polyolpolyallyl ether and mixtures of two or more of these compounds; and/or
(b) the cationic thickener copolymer has a structure of the formula (M3)

wherein $R^5$, $R^6$ and $R^7$, independently of one another, stand for a hydrogen atom or a methyl group x, A stands for ethane-1,2-diyl or propane-1,3-diyl, $Y^-$ stands for an anion.

10. The composition according to any one of points 1-9, characterized in that
(a) X in Formel (I) stands for ethane-1,2-diyl, propane-1,2-diyl, propane-1,3-diyl, butane-1,4-diyl, hexane-1,4-diyl or cyclohexane-1,4-diyl, preferably for butane-1,4-diyl, and/or
(b) R in formula (II) denotes a linear or branched C5 to C21-hydrocarbon radical with 0 to 3 double bonds, and/or
(c) said at least one cationic compound (EQ) is liquid to pasty at 20° C., and/or
(d) said at least one cationic compound (EQ) is present in an amount of about 2-60% by weight, preferably of about 2-30% by weight, based on the total amount of the liquid composition.

11. Liquid composition according to any one of the preceding points, characterized in that
(a) succinic acid, maleic acid, glutaric acid, adipic acid or mixtures thereof is selected as the dicarboxylic acid of the formula (I); and/or
(b) stearic acid, isostearic acid, palmitic acid, myristic acid, lauric acid, capric acid, caprylic acid, 2-ethylhexanoiuc acid, 2-octyldodecanoic acid, caproic acid, oleic acid, linoleic acid, linolenic acid, partially hydrogenated coconut fatty acid, palm fatty acid, palm kernel fatty acid, tallow fatty acid and mixtures of two or more of the aforementioned acids are selected as the monocarboxylic acid of the formula (II); and/or
(c) the molar ratio of the monocarboxylic acids (II) to the dicarboxylic acids (I) is in the range of 1:1 to 4:1, in particular preferably in the range of 1.5:1 to 3:1, and the molar ratio of the alkanolamines (III) to the sum of mono- and dicarboxylic acids is in the range of 1:1.2 to 1:2.4, in particular preferably in the range of about 1:1.5 to about 1:1.8.

12. Liquid composition according to any one of the preceding points, characterized in that dimethyl sulfate is used as the quaternizing agent.

13. Liquid composition according to any one of the preceding points, characterized in that the composition is a textile care agent, in particular a fabric softener.

14. Method for treating textiles, in which at least one textile is brought in contact with a liquid composition according to one of points 1 to 13.

15. Use of at least one liquid composition according to one of points 1 to 13 for care and/or conditioning of textile fabrics.

16. Method for producing a cationic compound (EQ) by reaction of
(i) a mixture of at least one dicarboxylic acid of the formula (I)

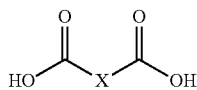

(I)

wherein X stands for a saturated or unsaturated hydrocarbon residue with 1 to 8 carbon atoms, and
at least one monocarboxylic acid of the formula (II)

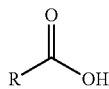

(II)

wherein R stands for a saturated or unsaturated hydrocarbon residue with 5 to 21 carbon atoms, with
(ii) at least one tertiary amine of the formula (III)

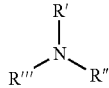

(III)

wherein R', R" and R'", independently of one another, stand for a ($C_2$ to $C_6$)-hydroxyalkyl group, in particular for 2-hydroxyethyl,
and then reacting the resulting product with
(iii) at least one quaternizing agent for quaternization of at least one amino group contained in the reaction product.

17. Method according to point 16, characterized in that the cationic compound (EQ) contains a compound of the formula (K1),

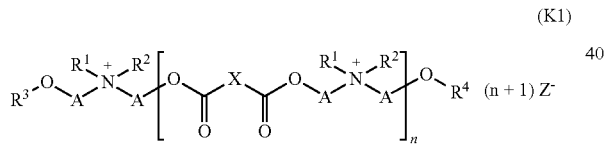

(K1)

wherein
X stands for a saturated or unsaturated hydrocarbon radical with 1 to 10 carbon atoms, in particular for butane-1,4-diyl,
A stands for a ($C_2$ to $C_6$)-alkanediyl group, in particular for ethane-1,2-diyl,
$R^1$ stands for a ($C_2$ to $C_4$)-hydroxyalkyl group or a ($C_6$ to $C_{22}$)-acyloxy-($C_2$ to $C_4$)-alkyl group, in particular for 2-hydroxyethyl or 2-(($C_6$ to $C_{22}$)-acyloxy)ethyl,
$R^2$ stands for methyl or ethyl,
$R^3$ and $R^4$, independently of one another, stand for a hydrogen atom or a ($C_6$ to $C_{22}$)-acyl group,
n stands for 1 or 2, and
$Z^-$ stands for an anion, in particular methyl sulfate,
with the provision that, according to formula (K1), at least one of the groups $R^1$, $R^3$ or $R^4$ includes a ($C_6$ to $C_{22}$)-acyl radical.

18. The method according to any one of points 16 or 17, characterized in that
(a) X in formula (I) stands for ethane-1,2-diyl, propane-1,2-diyl, propane-1,3-diyl, butane-1,4-diyl, hexane-1,4-diyl or cyclohexane-1,4-diyl, preferably for butane-1,4-diyl; and/or
(b) R in formula (II) denotes a linear or branched C5 to C21-hydrocarbon radical with 0 to 3 double bonds; and/or
(c) the cationic compound (EQ) is liquid to pasty at 20° C.

19. Method according to any one of points 16-18, characterized in that
(a) succinic acid, maleic acid, glutaric acid, adipic acid or mixtures thereof are selected as the dicarboxylic acid of the formula (I); and/or
(b) stearic acid, isostearic acid, palmitic acid, myristic acid, lauric acid, capric acid, 2-ethylhexanoic acid, 2-octyldodecanoic acid, caproic acid, oleic acid, linoleic acid, linolenic acid, partially hydrogenated coconut fatty acid, palm fatty acid, palm kernel fatty acid, tallow fatty acid and mixtures of two or more of the aforementioned acids are selected as the monocarboxylic acid of the formula (II); and/or
(c) the molar ratio of the monocarboxylic acids (II) to the dicarboxylic acids (I) is in the range of about 1:1 to about 4:1, in particular preferably in the range of about 1.5:1 to about 3:1, and the molar ratio of the alkanolamines (III) to the sum of mono- and dicarboxylic acids is in the range of about 1:1.2 to about 1:2.4, in particular preferably in the range of about 1:1.5 to about 1:1.8; and/or
(d) dimethyl sulfate is used as the quaternizing agent.

20. Cationic compound (EQ) obtainable by a method according to any one of points 16-19.

21. Use of a cationic compound (EQ) according to point 20 in a composition, in particular a liquid composition, for care and/or conditioning of textile fabrics.

22. Method for preparing clear liquid compositions, comprising the steps
(a) preparing an aqueous solution, containing the at least one first emulsifier at a temperature above 35° C., preferably above 40° C., and most especially preferably above 45° C.,
(b) adding the at least one cationic compound (EQ) as contemplated herein to the solution prepared in step a), wherein the temperature of the at least one cationic compound (EQ) or a preparation containing the at least one cationic compound (EQ), is between 30 and 65° C., preferably between 35 and 60° C. and most especially preferably between 40 and 55° C. during the addition.

23. Method for preparing a clear liquid composition containing at least one thickener, comprising the steps:
(a) preparing an aqueous solution, containing at least one thickener, at a temperature above 40° C., preferably above 50° C. and most especially preferably above 55° C., and
(b) adding the at least one first emulsifier as contemplated herein to the aqueous solution prepared in step (a), wherein the at least one first emulsifier or the composition, containing the at least one first emulsifier, is preheated to a temperature above 30° C., preferably above 35° C. and most especially preferably above 40° C.,
(c) adding the at least one cationic compound (EQ) as contemplated herein to the solution prepared in step (b), wherein the temperature of the at least one cationic compound (EQ) or a preparation containing the at least one cationic compound (EQ) is between 30 and 65° C., preferably between 35 and 60° C. and most especially preferably between 40 and 55° C. during the addition.

24. Method according to any one of points 22 or 23, characterized in that the aqueous solution in method step (a) comprises about 15 to about 70% by weight, preferably about 20 to about 60% by weight, more especially about 25 to about 50% by weight and most especially preferably about 30 to about 45% by weight water, wherein percent by weight is based on the clear liquid composition.

25. Method according to any one of points 22 to 24, characterized in that the solution obtained in step (b) of the method without a thickener and in step (c) of the method with a thickener is cooled by adding about 30 to about 85% by weight, preferably about 40 to about 80% by weight, more especially about 50 to about 75% by weight and most especially preferably about 55 to about 70% by weight water, wherein the percent by weight is based on the clear liquid composition, wherein the water is at a temperature of 10 to 29° C.

26. Method according to any one of points 23 to 25, characterized in that the at least one thickener in method step (a) of the method with a thickener is selected from the group consisting of neutral thickeners, cationic thickeners and mixtures thereof, wherein cationic thickeners are especially preferred.

27. Method according to point 23 to 26, characterized in that the at least one thickener is used in an amount of about 0.1 to about 10% by weight, wherein the percent by weight is based on the clear liquid composition.

The embodiments disclosed above in conjunction with the compositions as contemplated herein are readily also applicable to the methods and uses as contemplated herein and vice versa.

EXAMPLES

Example 1: Synthesis of the Cationic Ester Quat (EQ)

In a stirred heated reactor, 710.2 g stearic acid (technical grade) and 204.4 g adipic acid are placed together with 1.6 g hypophosphorous acid and heated to 70° C. After applying a slight vacuum (approx. 20-25 mbar), 360.3 g triethanolamine was added slowly within 1.5 h. At the same time the temperature was raised to 125° C. After the end of the dosing of triethanolamine, the reaction mixture was heated to 170° C. and stirred at this temperature for 2 hours. Next the mixture was cooled to 50° C. before adding 0.65 g of a 30% hydrogen peroxide solution.

For the quaternization, the batch was mixed with 300 mL propylene glycol while stirring. Then an amount of 446 g dimethyl sulfate was added over a period of approx. 2.5 h in such a manner that the temperature did not exceed 70° C. After the end of this addition the reaction mixture was stored for 2 hours at this temperature and then cooled to room temperature, yielding a product with a solids content of 80.5%.

Example 2: Formulation Examples

The claimed compositions are usually prepared as follows:
Starting with water, solids in a molten state are added to the water. For example, a pasty EQ is melted and thus rendered flowable before being added to the composition. If the compositions contain a thickener, it is the first ingredient to be added to the water at a temperature of 64° C. for example, having started with approx. 42% by weight water, where the percentage by weight is based on the clear liquid compositions. This can be accomplished with a Conti TDS machine (Ystral), for example. Then the thickener is allowed to swell for 30 to 120 minutes for example. Next the emulsifier(s) is/are added at a temperature of 55° C., for example. Then the ester quat is added at a temperature of 51° C. for example before cooling the resulting solution with approx. 58% by weight water based on the clear liquid compositions and then mixing this with solvent and preservative and homogenizing by stirring. Next coloring agents, perfume oils and enzyme mixture are added. The pH of the composition can be adjusted by means of citric acid.

Fabric softener formulations as contemplated herein:

|  | Formulation 1 | | Formulation 2 | | Formulation 3 | | Formulation 4 | |
| --- | --- | --- | --- | --- | --- | --- | --- | --- |
|  | % AS | t.q. | % AS | t.q. | % AS | t.q. | % AS | t.q. |
| Water | 91.19 | 90.66 | 90.19 | 89.42 | 88.44 | 87.42 | 61.69 | 54.38 |
| EQ from example 1 | 2 | 3 | 2 | 0 | 2 | 8 | 2 | 0 |
| Thickener (Rheovis CSP) | 2.000 | 2.484 | 3.000 | 3.727 | 4.000 | 4.969 | 30.00 | 37.26 |
| Emulsifier (Eumulgin CO40) | 0.600 | 0.600 | 0.600 | 0.600 | 0.600 | 0.600 | 0 | 7 |
|  | 2.500 | 2.500 | 2.500 | 2.500 | 3.250 | 3.250 | 0.600 | 0.600 |
| Solvent (propylene glycol) | 3.000 | 3.000 | 3.000 | 3.000 | 3.000 | 3.000 | 4.000 | 4.000 |
| Preservative | 0.005 | 0.050 | 0.005 | 0.050 | 0.005 | 0.050 | 3.000 | 3.000 |
| Coloring agent | 0.003 | 0.003 | 0.003 | 0.003 | 0.003 | 0.003 | 0.005 | 0.050 |
| Perfume oil | 0.70 | 0.70 | 0.70 | 0.70 | 0.70 | 0.70 | 0.003 | 0.003 |
|  |  |  |  |  |  |  | 0.70 | 0.70 |

Fabric softener formulations as contemplated herein:

|  | Formulation 5 | | Formulation 6 | | Formulation 7 | | Formulation 8 | |
| --- | --- | --- | --- | --- | --- | --- | --- | --- |
|  | % AS | t.q. | % AS | t.q. | % AS | t.q. | % AS | t.q. |
| Water | 91.19 | 90.66 | 90.19 | 89.42 | 88.44 | 87.42 | 61.69 | 54.38 |
| EQ from example 1 | 2 | 3 | 2 | 0 | 2 | 8 | 2 | 0 |
| Thickener (Jaguar HP105) | 2.000 | 2.484 | 3.000 | 3.727 | 4.000 | 4.969 | 30.00 | 37.26 |
| Emulsifier (Eumulgin CO40) | 0.600 | 0.600 | 0.600 | 0.600 | 0.600 | 0.600 | 0 | 7 |
|  | 2.500 | 2.500 | 2.500 | 2.500 | 3.250 | 3.250 | 0.600 | 0.600 |
| Solvent (propylene glycol) | 3.000 | 3.000 | 3.000 | 3.000 | 3.000 | 3.000 | 4.000 | 4.000 |
| Preservative | 0.005 | 0.050 | 0.005 | 0.050 | 0.005 | 0.050 | 3.000 | 3.000 |
|  | 0.003 | 0.003 | 0.003 | 0.003 | 0.003 | 0.003 | 0.005 | 0.050 |

-continued

|  | Formulation 5 | | Formulation 6 | | Formulation 7 | | Formulation 8 | |
| --- | --- | --- | --- | --- | --- | --- | --- | --- |
|  | % AS | t.q. | % AS | t.q. | % AS | t.q. | % AS | t.q. |
| Coloring agent | 0.70 | 0.70 | 0.70 | 0.70 | 0.70 | 0.70 | 0.003 | 0.003 |
| Perfume oil |  |  |  |  |  |  | 0.70 | 0.70 |

Comparative fabric softener formulations:

|  | Comparative formulation 1 | | Comparative formulation 2 | |
| --- | --- | --- | --- | --- |
|  | % AS | t.q. | % AS | t.q. |
| Water | 90.192 | 89.420 | 88.692 | 86.920 |
| EQ from example 1 | 3.000 | 3.727 | 3.000 | 3.727 |
| Thickener (Rheovis CSP) | 0.600 | 0.600 | 0.600 | 0.600 |
| Emulsifier (Dehydol LT5) | 2.500 | 2.500 | 0 | 0 |
| Solvent (propylene glycol) | 3.000 | 3.000 | 3.000 | 3.000 |
| Preservative | 0.005 | 0.050 | 0.005 | 0.050 |
| Coloring agent | 0.003 | 0.003 | 0.003 | 0.003 |
| Perfume oil | 0.70 | 0.70 | 0.70 | 0.70 |

The pH of all compositions is 2.0 to 3.5.

Jaguar HP-105, a nonionic thickener can be ordered from Rhodia.

Rheovis CSP, a cationic thickener can be ordered from BASF.

Eumulgin CO40 (100% AS) is a nonionic emulsifier that can be ordered from BASF. The HLB value is >14 (according to Griffin, see above).

Dehydol LT5 (100% AS) is a nonionic emulsifier that can be ordered from BASF. The HLB value is 10 (according to Griffin, see above).

Example 3: Storage Experiments

Formulation 2 according to the present disclosure (see above) was prepared as described in Example 2. The viscosity, density, pH and NTU value were determined on formulation 2. The NTU value was less than 30. The density of formulation 2 was approx. 1.007 g/cm3, the viscosity was approx. 230 mPas, the pH was approx. 3.25. Next, approx. 200 mL of formulation 2 was bottled in preparation jars (250 mL). In parallel with that, approx. 50 mL of formulation 2 was bottled in 100-mL screw cap glass containers. All the containers were sealed tightly and used in storage tests under the following five conditions: summer, fall or winter program (the temperature was controlled in the climate cabinet) or storage at a constant 40° C. or 60° C. (incubator). The specimens were stored for 24 weeks. The summer, fall and winter programs were cyclic temperature programs that were each different from the others. The program had the following temperature profiles:

| Time (hours) | Winter (° C.) | Fall (° C.) | Summer (° C.) |
| --- | --- | --- | --- |
| 0 | 0 | 10 | 24 |
| 12 | 0 | 10 | 24 |
| 17 | 5 | 20 | 32 |
| 29 | 5 | 20 | 32 |
| 34 | 10 | 30 | 40 |
| 46 | 10 | 30 | 40 |

-continued

| Time (hours) | Winter (° C.) | Fall (° C.) | Summer (° C.) |
| --- | --- | --- | --- |
| 51 | 5 | 20 | 32 |
| 63 | 5 | 20 | 32 |
| 68 | 0 | 10 | 24 |
| 80 | 0 | 10 | 24 |
| 85 | 10 | 30 | 40 |
| 97 | 10 | 30 | 40 |
| 102 | 5 | 20 | 32 |
| 114 | 5 | 20 | 32 |
| 119 | 10 | 30 | 40 |
| 131 | 10 | 30 | 40 |
| 136 | 0 | 10 | 24 |
| 148 | 0 | 10 | 24 |
| 153 | 5 | 20 | 32 |
| 165 | 5 | 20 | 32 |
| 168 | 0 | 10 | 24 |

The programs would begin again automatically after the time had elapsed.

Each week the formulation was inspected visually. This was done by taking a preparation glass containing the formulation from the climate cabinet/incubator, stored at approx. 23° C. for approx. 4 to 6 hours, and then the formulation was examined visually for its transparency. After the end of the 24-week storage test, the turbidity of the formulation was determined by determining the NTU value of the compositions.

After 4 weeks of storage in a winter and summer program, the storage test for the samples bottled in the 100-mL glass containers was terminated. The odor of each composition was tested by perfume specialists and evaluated. After each of the storage tests, formulation 2 did not have the odor of fatty acid.

With regard to the visual properties, formulation 2 according to the present disclosure still had NTU values of less than 30 after more than 24 weeks of storage under the conditions of the summer, winter and fall programs.

At 40° C. formulation 2 had an NTU value of less than 30 for up to 16 to 20 weeks.

At 60° C. formulation 2 had an NTU value of less than approx. 30 for up to 4 to 6 weeks.

In parallel and in an identical manner, the comparative formulation 2 was tested.

Comparative formulation 2 had an NTU value of at least 60 after at least 4 to 12 weeks in the summer program.

In the fall and winter program, comparative composition 2 had an NTU value of at least 60 after at most 8 to 12 weeks.

In storage at 40° C., comparative composition 2 had an NTU value of at least 60 after at most 4 to 12 weeks.

In storage at 60° C. comparative composition 2 had an NTU value of at least 60 after at most 2 weeks.

Example 4: Determination of Turbidity in Liquids (Turbidimetry)

The nephelometric turbidity unit (NTU) is often cited as a measured value for transparency. It is a unit for turbidity measurements in liquids that is used in water processing, for example. It is the unit of a turbidity of a liquid measured using a calibrated nephelometer. High NTU values are measured for cloudy liquids, whereas low values are determined for clear transparent liquids.

The turbidimeter of the HACH turbidimeter 2100Q type from the Hach Company, Loveland, Colo., USA was used with the calibration substances StablCal solution HACH (20 NTU), StablCal solution HACK (100 NTU) and StablCal solution HACH (800 NTU), all of which can also be ordered from the Hach Company. For these measurements, a 10-mL graduated cell with a cap was filled with the composition to be tested and the measurement was carried out at 20° C.

Already at an NTU value of 40, liquids can be perceived with the naked eye as being definitely cloudy.

Example 5: Density Determination

The density was determined using the DMA 4100 M device from the company Anton Paar at 20° C.

Example 6: Viscosity Determination

The viscosities of the compositions tested were determined using an RV DV II Brookfield viscometer at 20 rpm and 20° C. using spindle 2.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A liquid composition comprising
(a) water,
(b) at least one cationic compound (EQ) obtainable by reaction of
(i) a mixture of at least one dicarboxylic acid of formula (I)

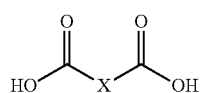

where X stands for a saturated or unsaturated hydrocarbon radical with 1 to 8 carbon atoms, and
at least one monocarboxylic acid of formula (II)

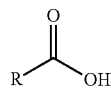

where R stands for a saturated or unsaturated hydrocarbon radical with 5 to 21 carbon atoms, with (ii) at least one tertiary amine of formula (III)

where R', R" and R"', independently of one another, stand for a (C2 to C6) hydroxyalkyl group,
with the resulting product reacted with
(iii) at least one quaternizing agent for quaternization of at least one amino group contained in the reaction product of (i) and (ii), and
(c) at least one first nonionic emulsifier selected from the group consisting of addition products of 15 to 60 mol ethylene oxide, castor oil, hydrogenated castor oil, and mixtures thereof, having an HLB value of at least 14.0,
(d) at least one thickener selected from the group consisting of neutral thickeners, cationic thickeners, and mixtures thereof;
wherein in the composition the ratio of (c) to (b) is at least 0.5: 1,
wherein the liquid composition has a pH (25° C.) between about 1 and about 4.5, and
wherein the liquid composition is a transparent textile care agent such that the liquid composition has a nephelometric turbidity unit (NTU) value of 30 or less as determined at 20° C.

2. The liquid composition according to claim 1, wherein:
the amount of (b) in the composition amounts to about 0.1-30% by weight, and/or
the amount of (c) in the composition is about 0.1 to about 50% by weight, and
the liquid composition comprises enzyme mixture with an amount of 0.01-5.0% by weight, based on the total weight of the liquid composition.

3. The liquid composition according to claim 1, wherein the composition has at least one second nonionic emulsifier, wherein the HLB value of an emulsified mixture of the at least one first and at least one second nonionic emulsifier amounts to at least about 12.0.

4. The liquid composition of claim 3, wherein the at least one nonionic emulsifier (c) is selected from the group consisting of addition products of 40 to 60 mol ethylene oxide with an HLB value of at least 14.0.

5. The liquid composition according to claim 1, wherein the at least one first nonionic emulsifier (c) is selected from the group consisting of addition products of 40 to 60 mol of ethylene oxide, castor oil, hydrogenated castor oil and mixtures thereof, having an HLB value of at least 14.0.

6. The liquid composition of claim 5, wherein the thickener is present in an amount of about 0.1-10% by weight based on the total weight of the liquid composition.

7. The liquid composition of claim 5, wherein the thickener is selected from the group consisting of neutral thickeners, cationic thickeners and mixtures thereof.

8. The liquid composition according to claim 1, wherein the at least one thickener is chosen from at least one nonionic thickener selected from the group consisting of hydroxyethyl cellulose (HEC), hydroxypropyl cellulose (HPC), hydroxypropylmethyl cellulose (HPMC) and methyl cellulose (MC), guar, guar derivatives and mixtures of the aforementioned nonionic thickeners.

9. The liquid composition according to claim 1, wherein the at least one thickener is chosen from at least one cationic thickener comprising a copolymer of at least one monomer of the formula (M1) and at least one monomer of formula (M2)

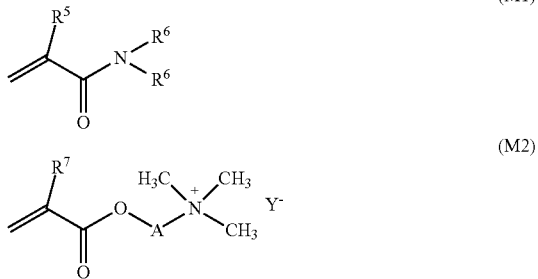

where R5, R6 and R7 independently of one another stand for a hydrogen atom or a methyl group,
A stands for ethane-1,2-diyl or propane-1,3-diyl,
Y stands for an anion.

10. The liquid composition according to claim 9, wherein
(a) R6 according to formula (M1) stands for a hydrogen atom; and/or
(b) R5 according to formula (M1) stands for a hydrogen atom; and/or
(c) A according to formula (M2) stands for ethane-1,2-diyl or propane-1,3-diyl; and/or
(d) said cationic thickener copolymer is obtained in the amount of about 95 to about 100% by weight from the monomers of formula (M1) and (M2), based on the total weight of the copolymer; and/or
(e) said cationic thickener copolymer is covalently crosslinked; and/or
(f) said cationic thickener copolymer is obtained by emulsion polymerization; and/or
(g) said cationic thickener copolymer is present in the form of beads; and/or
(h) said cationic thickener copolymer is present in a total amount of about 0.05 to about 2.0% by weight.

11. The liquid composition according to claim 9, wherein
(a) said cationic thickener copolymer is covalently crosslinked by using at least one copolymerizable crosslinking agent with at least two ethylenically unsaturated groups; and/or
(b) the cationic thickener copolymer has a structure according to formula (M3)

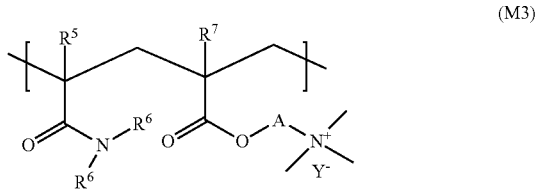

where R5, R6 and R7, independently of one another, stand for a hydrogen atom or a methyl group, A stands for ethane-1,2-diyl or propane-1,3-diyl, and Y− stands for an anion.

12. The liquid composition of claim 11, wherein said at least one copolymerizable crosslinking agent is chosen from divinylbenzene, tetraallylammonium chloride, allyl acrylate, allyl methacrylate, diacrylate compounds of glycols, diacrylate compounds of polyglycols, dimethacrylate compounds of glycols, dimethacrylate compounds of polyglycols, butadiene, 1,7 octadiene, allylacrylamide, allylmethacrylamide, bisacrylamidoacetic acid, N,N'-methylene-bisacrylamide, polyol polyallyl ether and mixtures of two or more of these compounds.

13. The liquid composition according to claim 1, wherein
(a) X in formula (I) stands for ethane-1,2-diyl, propane-1,2-diyl, propane-1,3-diyl, butane-1,4-diyl, hexane-1,4-diyl or cyclohexane-1,4-diyl, and/or
(b) R in formula (II) denotes a linear or branched C5 to C21 hydrocarbon radical with 0 to 3 double bonds, and/or
(c) said at least one cationic compound (EQ) is liquid to pasty at 20° C., and/or
(d) said at least one cationic compound (EQ) is present in an amount of about 2-60% by weight, based on the total amount of the liquid composition.

14. The liquid composition according to claim 1, wherein the liquid composition is a fabric softener.

15. The liquid composition according to claim 1, wherein the at least one first emulsifier (c) is a nonionic emulsifier with an HLB value of at least 15.0, wherein the ratio of (c) to (b) in the liquid composition amounts to at least about 2:1, wherein the amount of (b) in the composition amounts to about 2-10% by weight, and wherein the amount of (c) in the composition is about 2 to 10% by weight, based on the total weight of the liquid composition.

16. The liquid composition according to claim 1, wherein the liquid composition is a fabric softener, and wherein the mixture of the at least one dicarboxylic acid of formula (I) and the at least one monocarboxylic acid of formula (II) is provided with a monocarboxylic acid of formula (II) : dicarboxylic acid of formula (I) molar ratio of from about 1.5:1 to about 3:1.

17. The liquid composition according to claim 16, wherein the mixture of the at least one dicarboxylic acid of formula (I) and the at least one monocarboxylic acid of formula (II) and the at least one tertiary amine of formula (III) are provided with a tertiary amine of formula (III) : mixture of acids of formula (I) and formula (II) molar ratio of from about 1:1.2 to about 1:2.4.

18. The liquid composition according to claim 17, wherein the tertiary amine of formula (III) : mixture of acids of formula (I) and formula (II) molar ratio is from about 1:1.5 to about 1:1.8.

19. A liquid composition comprising:
(a) water,
(b) at least one cationic compound (EQ) obtainable by reaction of
(i) a mixture of at least one dicarboxylic acid of formula (I)

where X stands for a saturated or unsaturated hydrocarbon radical with 1 to 8 carbon atoms, and (ii) at least one monocarboxylic acid of formula (II)

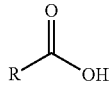
(II)

where R stands for a saturated or unsaturated hydrocarbon radical with 5 to 21 carbon atoms, with
(ii) at least one tertiary amine of formula (III)

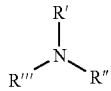
(III)

where R', R" and R"", independently of one another, stand for a (C2 to C6) hydroxyalkyl group,
with the resulting product reacted with
(iii) at least one quaternizing agent for quaternization of at least one amino group contained in the reaction product of (i) and (ii), and
(c) at least one first emulsifier, wherein the at least one first emulsifier is a nonionic emulsifier with an HLB value of at least 12.0 selected from the group consisting of addition products of 15 to 60 mol ethylene oxide, castor oil, hydrogenated castor oil, and mixtures thereof,
wherein the liquid composition has a pH (25° C.) between about 1 and about 4.5, wherein the at least one cationic compound (EQ) (b) comprises a compound of formula (K1):

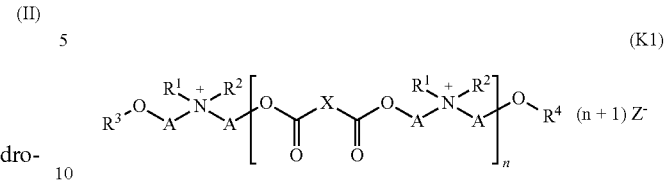
(K1)

where
X stands for a saturated or unsaturated hydrocarbon radical with 1 to 10 carbon atoms,
A stands for a (C2 to C6) alkanediyl group,
R1 stands for a (C2 to C4) hydroxyalkyl group or a (C6 to C22) acyloxy-(C22 to C4) alkyl group,
R2 stands for methyl or ethyl,
R3 and R4 independently of one another stand for a hydrogen atom or a (C6 to C22) acyl group,
n stands for 1 or 2 and
Z– stands for an anion,
with the provision that, according to formula (K1), at least one of the groups R1, R3 or R4 comprises a (C6 to C22) acyl radical.

20. The liquid composition of claim 19, wherein:
X stands for butane-1,4-diyl,
A stands for ethane-1,2-diyl,
R1 stands for 2-hydroxyethyl or 2-((C6 to C22)-acyloxy) ethyl, and
Z– stands for methyl sulfate.

* * * * *